United States Patent
Zhu et al.

(10) Patent No.: US 11,053,185 B2
(45) Date of Patent: Jul. 6, 2021

(54) DENDRITIC POLYETHYLENE GLYCOL DERIVATIVE, AND PREPARATION METHOD AND APPLICATION THEREOF

(71) Applicant: JENKEM TECHNOLOGY CO., LTD. (TIANJIN), Tianjin (CN)

(72) Inventors: Hui Zhu, Tianjin (CN); Meina Lin, Tianjin (CN); Xuan Zhao, Tianjin (CN)

(73) Assignee: JENKEM TECHNOLOGY CO., LTD. (TIANJIN), Tianjin (CN)

( * ) Notice: Subject to any disclaimer, the term of this patent is extended or adjusted under 35 U.S.C. 154(b) by 0 days.

(21) Appl. No.: 16/729,882

(22) Filed: Dec. 30, 2019

(65) Prior Publication Data
US 2020/0131107 A1    Apr. 30, 2020

Related U.S. Application Data

(63) Continuation of application No. PCT/CN2018/093134, filed on Jun. 27, 2018.

(30) Foreign Application Priority Data

Jun. 28, 2017 (CN) .......................... 201710513034.4
Nov. 30, 2017 (CN) .......................... 201711241222.2

(51) Int. Cl.
*C07C 43/11* (2006.01)
*A61K 47/60* (2017.01)
*C07C 217/08* (2006.01)
*C07C 233/56* (2006.01)

(52) U.S. Cl.
CPC .............. *C07C 43/11* (2013.01); *A61K 47/60* (2017.08); *C07C 217/08* (2013.01); *C07C 233/56* (2013.01)

(58) Field of Classification Search
CPC ....... C07C 43/11; C07C 217/08; C07C 41/30; C07C 233/56
See application file for complete search history.

(56) References Cited

FOREIGN PATENT DOCUMENTS

| CN | 103304804 A | * | 9/2013 |
| CN | 106496587 A | * | 3/2017 |

* cited by examiner

*Primary Examiner* — Rosalynd A Keys
(74) *Attorney, Agent, or Firm* — Flener IP & Business Law; Zareefa B. Flener

(57) ABSTRACT

The disclosure discloses a dendritic polyethylene glycol derivative and a preparation method and an application thereof. The dendritic polyethylene glycol derivative has a structure of formula (I), has multiple end functional groups, has a stronger water solubility in comparison with linear-chain polyethylene glycol, and can solve a problem of insufficient water solubility due to the increase of load when modifying an insoluble drug by the polyethylene glycol. The preparation method of the dendritic polyethylene glycol derivative provided by the disclosure has mild reaction conditions, is green and environmentally friendly, is low in cost, and is easy to implement industrialization.

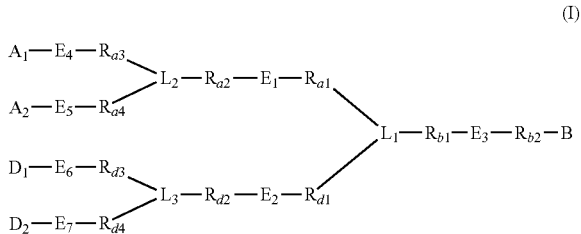

(I)

14 Claims, 6 Drawing Sheets

DENDRITIC POLYETHYLENE GLYCOL DERIVATIVE, AND PREPARATION METHOD AND APPLICATION THEREOF

CROSS-REFERENCE TO RELATED APPLICATION

This application is a continuation application of International patent application No. PCT/CN2018/093134, filed on Jun. 27, 2018, which claims priority to Chinese patent application No. CN201711241222.2, filed on Nov. 30, 2017, and Chinese patent application No. CN201710513034.4, filed on Jun. 28, 2017. All of the aforementioned patent applications are hereby incorporated by reference in their entireties.

TECHNICAL FIELD

The disclosure relates to the field of chemical technologies, in particular to a dendritic polyethylene glycol derivative, and a preparation method and an application thereof.

BACKGROUND

A dendrimer is a kind of non-linear polymer with a highly branched structure, the structure of which has excellent geometric symmetry. Moreover, the volume and shape of molecules of the dendrimer can be accurately controlled. Due to the unique structure of the dendrimer, it has a series of unique physical and chemical properties such as low viscosity, high rheological property, and containing a large number of end functional groups, which are not available in traditional linear polymers, and has a wide application prospect in such fields as supramolecular chemistry, biomedicine, photochemistry, electrochemistry, catalyst, etc.

However, the dendrimers that have been successfully prepared at present still have some deficiencies:

(1) Toxicity of the Dendrimer Containing a Large Amount of N Atoms

Taking an polyamidoamine dendrimer (PAMAM) as an example, the PAMAM will form cations after entering an organism since it contains a large number of N atoms, while interactions between the cations, especially cations on surfaces of macromolecules, and anions on surfaces of cell membranes destroy a biochemical environment of cells, thus showing certain toxicity;

(2) Biodegradability of the Dendrimer Containing Aromatic Rings

Taking a glutamic acid-alanine dipeptide dendrimer as an example, a glutamic acid is taken as a constituent part of a repeating unit, and the higher a number of generations of the synthesized dendrimer, the more aromatic rings are carried, and the aromatic rings are difficult to be rapidly degraded and completely discharged in an organism, thus a retention time in the organism becomes longer, which is unfavorable to the health of the organism; and (3) Compatibility with Hydrophilic and Strongly Polar Carriers A majority of the existing dendrimers exhibit a hydrophobic property, which limits the dendrimers to be jointly applied with a large number of hydrophilic and strongly polar drugs; although a grafting problem can be solved by surface modification of polyethylene glycol, an internal hydrophobic space of the dendrimer is not utilized, and unique wrapping and loading functions of the dendrimer are wasted.

Polyethylene glycol (PEG) is a kind of polyethylene polymer compound with extremely wide applications, which can be dissolved in water and multiple solvents. Due to excellent water solubility and biocompatibility, and no immunogenicity thereof, PEG is often used to modify insoluble drugs to increase water solubility of the drugs. Some studies have reported that PEG40k was used to modify a 20-hydroxyl of camptothecin. The water solubility of the modified PEG-camptothecin was about 2 mg/mL, which was 800 times that of the original camptothecin (0.0025 mg/mL). The lactone and the tertiary alcohol at position 20 in a camptothecin structure are both basic active sites for inhibiting topoisomerases. PEG modification on the 20-hydroxyl improves the stability of lactone and endows the drug with anti-tumor targeting while improving the water solubility of the drug. It has been found through animal experiments that a concentration of a prodrug in a tumor site is 30 times higher than the camptothecin, greatly improving a curative effect thereof. At present, the drug has entered clinical trials. In addition to the camptothecin, PEG modification on paclitaxel, scutellarin, etc., can also greatly enhance the water solubility thereof and improve oil-water distribution, thus increasing the curative effect. The prodrugs of paclitaxel, adriamycin, cytarabine, etc., modified by the PEG have also entered clinical trials.

The inventors of the present invention prepare a dendritic polyethylene glycol derivative through experiments and researches, which has good water solubility and biocompatibility and very low toxicity, and can be used as a carrier to modify an insoluble drug to improve the water solubility of the drug; meanwhile, the dendritic polyethylene glycol derivative has a plurality of end functional groups, so that the drug load can be increased and the bioavailability of the drug can be improved.

SUMMARY

The disclosure provides a dendritic polyethylene glycol derivative having a structure of formula (I):

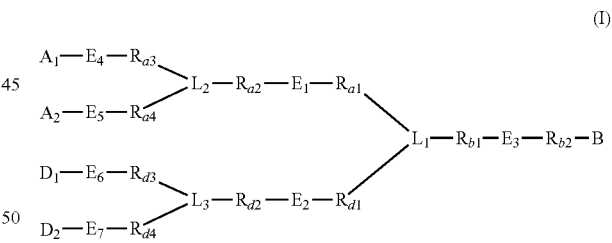

(I)

wherein, $A_1$, $A_2$, $D_1$ and $D_2$ are Y—X-structures, which are the same or different, or

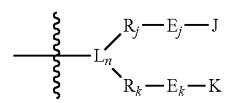

structures, which are the same or different; and J and K are Y—X-structures, which are the same or different;

$R_{a1\text{-}4}$, $R_{b1\text{-}2}$ and $R_{d1\text{-}4}$ (i.e., $R_{a1}$, $R_{a2}$, $R_{a3}$, $R_{a4}$, $R_{b1}$, $R_{b2}$, $R_{d1}$, $R_{d2}$, $R_{d3}$ and $R_{d4}$), as well as $R_j$ and $R_k$ are linking groups independently selected from one or a combination of several of —(CH$_2$)$_r$—, —(CR$_1$R$_2$)$_r$—, —(CH$_2$)$_r$NH—, —NHCO(CH$_2$)$_r$—, —(CH$_2$)$_r$CONH— and —CO(CH$_2$)$_r$—, and r is an integer of 0 to 30 (specifically like 0, 1, 2, 3, 4, 5, 6, 7, 8, 9, 10, 15, 20, 25 or 30), R$_1$ and R$_2$ are independently selected from one or a combination of several of —H, C1-C6 alkyl, —OR', —NHR', —N(R')$_2$, —CN, —F, —Cl, —Br, —I, —COR', —COOR', —OCOR', —CONHR' and —CON(R')$_2$, R' is selected from —H, C1-C6 alkyl, —F, —Cl, —Br and —I, and B is a Y—X-structure, which is the same as or different from A$_1$, A$_2$, D$_1$, D$_2$, J and K;

X is a linking group selected from one or a combination of more than two of —(CH$_2$)$_i$—, —(CH$_2$)$_i$NH—, —CO(CH$_2$)$_i$—, —(CH$_2$)$_i$OCOO—, —(CH$_2$)$_i$OCONH—, —(CH$_2$)$_i$NHCONH—, —OC(CH$_2$)$_i$COO—, —(CH$_2$)$_i$COO— and —(CH$_2$)$_i$CONH—, and i is an integer of 0 to 10 (specifically 0, 1, 2, 3, 4, 5, 6, 7, 8, 9 or 10);

Y is an end group selected from one of C1-C6 alkyl, C1-C6 alkoxy, H (hydrogen atom), hydroxyl, amino, aminomethyl, maleimide group, carboxyl, ester, sulfydryl, succinimidyl carbonate, succinimidyl acetate, succinimidyl propionate, succinimidyl succinate, succinimidyl, dithiopyridyl, propionic acid, aldehyde group, thioester group, acrylic group, acryloxy, azido, glutaric group, hydrazide, alkynyl, p-nitrophenyl carbonate, isocyanato, silane group, carboxymethyl, vinyl sulfone group and vitamin H residue;

E$_{1-7}$, E$_j$ and E$_k$ are polyethylene glycol groups (OCH$_2$CH$_2$)$_m$, which are the same or different, and m is an integer of 0 to 100 (specifically like 0 to 20 (such as 0, 1, 2, 3, 4, 5, 6, 7, 8, 9, 10, 11, 12, 13, 14, 15, 16, 17, 18, 19 or 20), 30 to 50 (such as 30, 35, 40, 45 or 50) or 50 to 100 (such as 50, 60, 70, 80, 90 or 100));

L$_{1-3}$ and L$_n$ are branching points independently selected from one or a combination of more than two of structures of formulae (II) to (VIII):

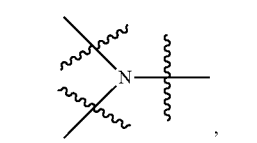
(II)

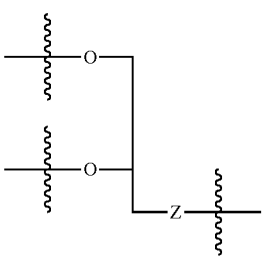
(III)

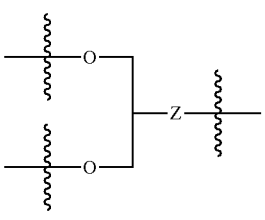
(IV)

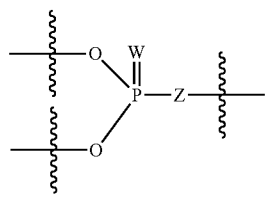
(V)

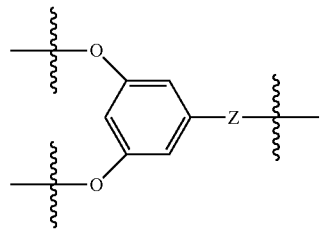
(VI)

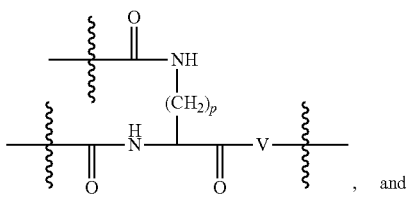
(VII)
, and

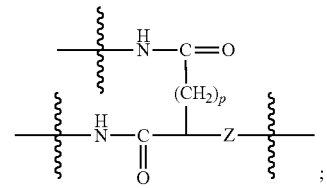
(VIII)
;

Z is selected from one of O, S, NH, NHCO, CO, COO, OC(O) and (CH$_2$)$_s$, and s is an integer of 0 to 10 (specifically like 0, 1, 2, 3, 4, 5, 6, 7, 8, 9 or 10);

p is an integer of 0 to 10 (specifically like 0, 1, 2, 3, 4, 5, 6, 7, 8, 9 or 10);

W is O or S; and

V is O or NH.

In an example of the disclosure, the R$_{a1}$, the R$_{a2}$, the R$_{a3}$, the R$_{a4}$, the R$_{b1}$, the R$_{b2}$, the R$_{d1}$, the R$_{d2}$, the R$_{d3}$, the R$_{d4}$, the R$_j$ and the R$_k$ are —(CH$_2$)$_r$—, which are the same or different, and r is selected from an integer of 0 to 10, and more preferably an integer of 0 to 5, such as 0, 1, 2, 3, 4 and 5.

In a preferred example of the disclosure, the A$_1$, the A$_2$, the D$_1$, the D$_2$ and the B are Y—X-structures, which are the same or different, and the dendritic polyethylene glycol derivative is a four-arm dendritic polyethylene glycol derivative.

In another preferred example of the disclosure, the A$_1$, the A$_2$, the D$_1$ and the D$_2$ are

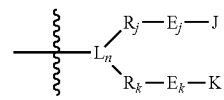

structures, which are the same or different, and the dendritic polyethylene glycol derivative may be an eight-arm dendritic polyethylene glycol derivative.

Based on the prior art and the disclosure, those skilled in the art may adopt a branched structure (such as

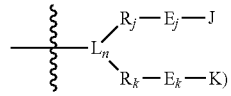

to B, and may also obtain six-arm, eight-arm, ten-arm dendritic polyethylene glycol derivatives or the like. Any modifications, and equivalent substitutions, etc. made within the spirit and principle of the disclosure without inventive work shall be included in the scope of protection of the disclosure.

Specifically, the X is selected from one or a combination of several of $-(CH_2)_i-$, $-CO(CH_2)_i-$, $-(CH_2)_iNH-$ and $(CH_2)_iCONH-$; and is preferably $-(CH2)_i-$.

Specifically, i in the linking group X is 0, 1, 2, 3 or 4.

In a preferred example of the disclosure, the X is a single bond, $-CH_2-$, $-CH_2CH_2-$ or $-CH_2CH_2CH_2-$.

In an example of the disclosure, the Y is selected from one of methoxy, hydroxyl, amino, azido, sulfydryl, carboxyl, ester, aldehyde group, acrylic group and maleimide group.

In a preferred example of the disclosure, the $A_1$, the $A_2$, the $D_1$ and the $D_2$ are independently selected from one of $-H$, $-CH_3$, $-OCH_3$, $-OH$, $-NH_2$, $-CH_2NH_2$, $-CH_2CH_2NH_2$, $-N_3$, $-CH_2N_3$, $-CH_2CH_2N_3$, $-CH_2COOH$, $-CH_2CH_2COOH$, $-SH$, $-CH_2CH_2CHO$ and $-CH_2CH_2CH_2CHO$.

In a more preferred example of the disclosure, the $A_1$, the $A_2$, the $D_1$ and the $D_2$ are independently selected from one of $-CH_3$, $-OCH_3$, $-CH_2CH_2NH_2-$, $-CH_2CH_2COOH$ and $-CH_2CH_2N_3$.

In a preferred example of the disclosure, the B is selected from one of $-H$, $-OH$, $-NH_2$, $-CH_2COOH$, $-CH_2CH_2COOH$, $-SH$, $-CH_2CH_2CHO$ and $-CH_2CH_2CH_2CHO$.

Specifically, m in the polyethylene glycol group $(OCH_2CH_2)_m$ is an integer of 0 to 20, and preferably an integer of 0 to 12; and more specifically, m is 0, 1, 2, 3, 4, 5, 6, 7 or 8;

specifically, the Z is selected from one of O, NH, NHCO and $(CH_2)_s$, and more specifically, O or NHCO;

specifically, s is an integer of 0 to 5, for example, 0, 1, 2, 3, 4 or 5; and specifically, s is an integer of 0 to 5, for example, 0, 1, 2, 3, 4 or 5.

In a preferred example of the disclosure, the $L_{1-3}$ and the $L_n$ have structures of formula (II) or formula (III).

In a more preferred example of the disclosure, the $L_1$-3 and the $L_n$ are independently selected from

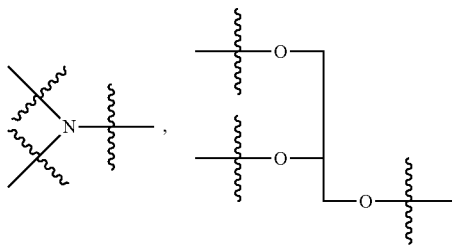

-continued

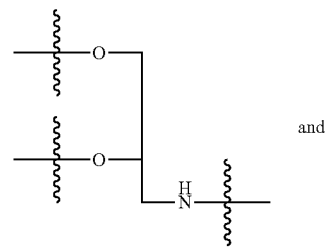

and

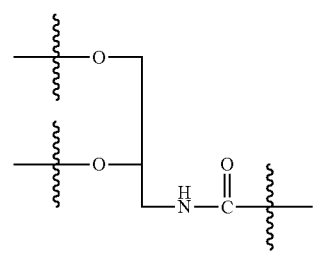

In an example of the disclosure, the dendritic polyethylene glycol derivative has a structure as follows:

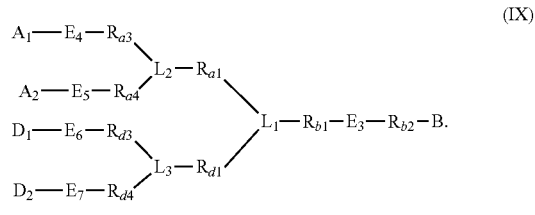

(IX)

In another example of the disclosure, the dendritic polyethylene glycol derivative has a structure as follows:

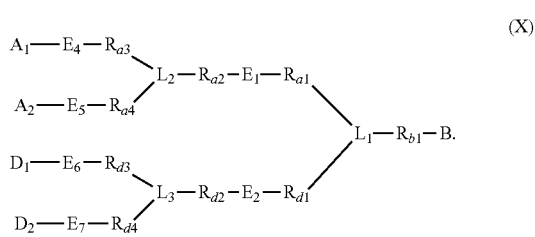

(X)

In another example of the disclosure, the dendritic polyethylene glycol derivative has a structure as follows:

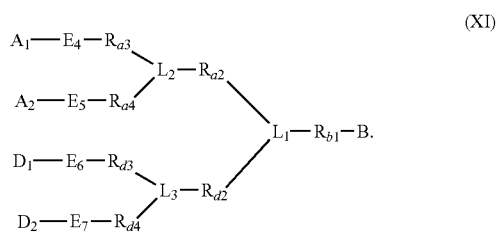

(XI)

In another example of the disclosure, the dendritic polyethylene glycol derivative has a structure as follows:

(XII)

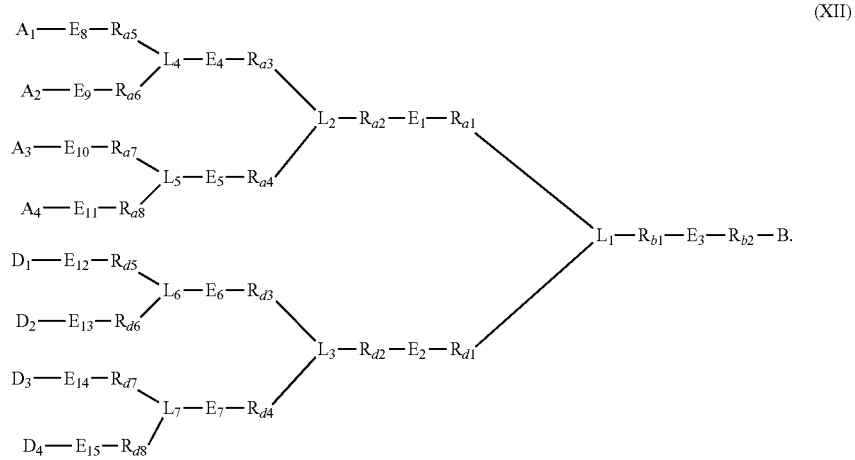

The linking groups R ($R_{a1}$, $R_{a2}$, $R_{a3}$, $R_{a4}$, $R_{a5}$, $R_{a6}$, $R_{a7}$, $R_{a8}$, $R_{b1}$, $R_{b2}$, $R_{d1}$, $R_{d2}$, $R_{d3}$, $R_{d4}$, $R_{d5}$, $R_{d6}$, $R_{d7}$ and $R_{d8}$), the branching points L ($L_1$, $L_2$, $L_3$, $L_4$, $L_5$, $L_6$ and $L_7$), the polyethylene glycol groups E ($E_{1-15}$), and the groups $A_1$, $A_2$, $A_3$, $A_4$, $D_1$, $D_2$, $D_3$, $D_4$ and B in the above formulae IX to XII have the above corresponding definitions of the disclosure.

Specifically, in the formulae IX to XII, the $R_{a1}$, the $R_{a2}$, the $R_{a3}$, the $R_{a4}$, the $R_{a5}$, the $R_{a6}$, the $R_{a7}$, the $R_{a8}$, the $R_{b1}$, the $R_{b2}$, the $R_{d1}$, the $R_{d2}$, the $R_{d3}$, the $R_{d4}$, the $R_{d5}$, the $R_{d6}$, the $R_{d7}$ and the $R_{d8}$ are —$(CH_2)_r$—, which are the same or different, and r is selected from an integer of 0 to 10, and more preferably an integer of 0 to 5, such as 0, 1, 2, 3, 4 and 5.

Specifically, in the formulae IX to XII, the $L_1$, the $L_2$, the $L_3$, the $L_4$, the $L_5$, the $L_6$ and the $L_7$ have structures of the formula (II) or the formula (III), and more preferably, are selected from

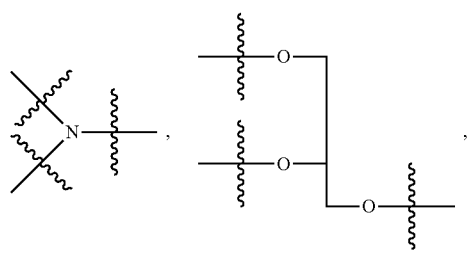

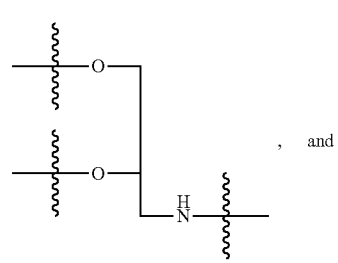, and

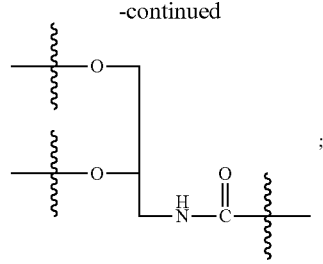

specifically, for the formulae IX to XII, m in the polyethylene glycol group $OCH_2CH_2)_m$ is an integer of 0 to 20, more preferably an integer of 0 to 12, and most preferably, the m is 0, 1, 2, 3, 4, 5, 6, 7 or 8.

Specifically, for the formulae IX to XII, in the $A_1$, the $A_2$, the $D_1$, the $D_2$ and the B, X is selected from one or a combination of several of —$(CH_2)_i$—, —$CO(CH_2)_i$—, —$(CH_2)_iNH$— and $(CH_2)_iCONH$—, and more preferably —$(CH_2)_i$; preferably, i in the linking group X is 0, 1, 2, 3 or 4; further preferably, the X is a single bond, —$CH_2$—, —$CH_2CH_2$— or —$CH_2CH_2CH_2$—.

Specifically, for the formulae IX to XII, in the $A_1$, the $A_2$, the $D_1$, the $D_2$ and the B, the Y is selected from one of methoxy, hydroxyl, amino, azido, sulfydryl, carboxyl, ester, aldehyde group, acrylic group and maleimide group.

More specifically, in the formulae IX to XII, the $A_1$, the $A_2$, the $D_1$ and the $D_2$ are independently selected from one of —H, —$CH_3$, —$OCH_3$, —OH, —$NH_2$, —$CH_2NH_2$, —$CH_2CH_2NH_2$, —$N_3$, —$CH_2N_3$, —$CH_2CH_2N_3$, —$CH_2COOH$, —$CH_2CH_2COOH$, —SH, —$CH_2CH_2CHO$ and —$CH_2CH_2CH_2CHO$; more specifically, the $A_1$, the $A_2$, the $D_1$ and the $D_2$ are independently selected from one of —$CH_3$, —$OCH_3$, —$CH_2CH_2NH_2$—, —$CH_2CH_2COOH$ and —$CH_2CH_2N_3$.

Specifically, in the formulae IX to XII, the B is selected from one of —H, —OH, —$NH_2$, —$CH_2COOH$, —$CH_2CH_2COOH$, —SH, —$CH_2CH_2CHO$ and —$CH_2CH_2CH_2CHO$.

In a specific example of the disclosure, the dendritic polyethylene glycol derivative has a structure as follows:

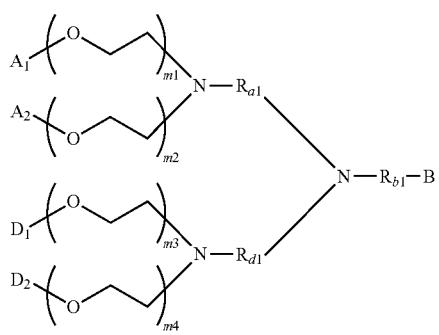

(XIII)

wherein, the $R_{a1}$, the $R_{b1}$, the $R_{d1}$, the $A_1$, the $A_2$, the $D_1$, the $D_2$ and the B have the above definitions of the disclosure; and m1-4 are independently selected from an integer of 0 to 100, specifically like an integer of 0 to 20, and especially an integer of 0 to 12; in an example of the disclosure, all the m1-4 are 3.

Specifically, for the formula XIII, in the $A_1$, the $A_2$, the $D_1$, the $D_2$ and the B, the X is selected from one or a combination of several of —$(CH_2)_i$—, —$CO(CH_2)_i$—, —$(CH_2)_iNH$— and $(CH_2)_iCONH$—, and more specifically —$(CH_2)_i$—; specifically, i in the linking group X is 0, 1, 2, 3 or 4; and in an example of the disclosure, X is a single bond, —$CH_2$—, —$CH_2CH_2$— or —$CH_2CH_2CH_2$—.

Specifically, for the formula XIII, in the $A_1$, the $A_2$, the $D_1$, the $D_2$ and the B, the Y is selected from one of methoxy, hydroxyl, amino, azido, sulfydryl, carboxyl, ester, aldehyde group, acrylic group and maleimide group.

More specifically, in the formula XIII, the $A_1$, the $A_2$, the $D_1$ and the $D_2$ are independently selected from one of —H, —$CH_3$, —$OCH_3$, —OH, —$NH_2$, —$CH_2NH_2$, —$CH_2CH_2NH_2$, —$N_3$, —$CH_2N_3$, —$CH_2CH_2N_3$, —$CH_2COOH$, —$CH_2CH_2COOH$, —SH, —$CH_2CH_2CHO$ and —$CH_2CH_2CH_2CHO$; further specifically, the $A_1$, the $A_2$, the $D_1$ and the $D_2$ are independently selected from one of —$CH_3$, —$OCH_3$, —$CH_2CH_2NH_2$, —$CH_2CH_2COOH$ and —$CH_2CH_2N_3$; and in an example of the disclosure, the $A_1$, the $A_2$, the $D_1$ and the $D_2$ are all —$CH_3$.

More specifically, in the formula XIII, the B is selected from one of —H, —OH, —$NH_2$, —$CH_2COOH$, —$CH_2CH_2COOH$, —SH, —$CH_2CH_2CHO$ and —$CH_2CH_2CH_2CHO$; and in an example of the disclosure, the B is —OH.

Specifically, in the formula XIII, the $R_{a1}$, the $R_{b1}$ and the $R_{d1}$ are —$(CH_2)_r$—, which are the same or different, and r is selected from an integer of 0 to 10, and more specifically, the $R_{a1}$, the $R_{b1}$ and the $R_{d1}$ are —$(CH_2)_r$—, which are the same or different, and r is selected from an integer of 0 to 5; and in an example of the disclosure, the $R_{a1}$, the $R_{b1}$ and the $R_{d1}$ are all —$C_3H_6$—.

More specifically, in the formula XIII, the —$R_{b1}$—B is —$C_3H_6$—OH.

In an example of the disclosure, the dendritic polyethylene glycol derivative has a structure as follows:

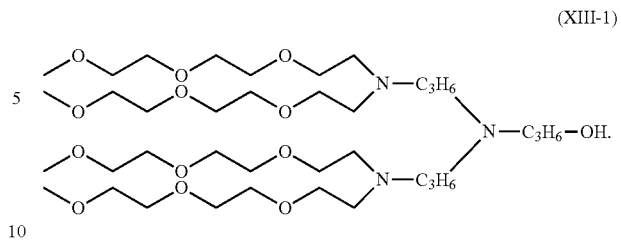

(XIII-1)

In a specific example of the disclosure, the dendritic polyethylene glycol derivative has a structure as follows:

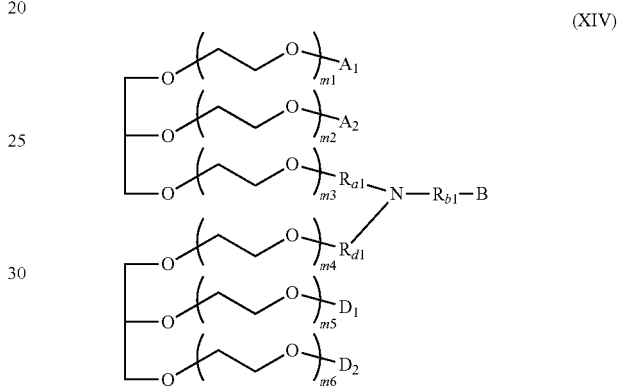

(XIV)

wherein, the $R_{a1}$, the $R_{b1}$, the $R_{d1}$, the $A_1$, the $A_2$, the $D_1$, the $D_2$ and the B have the above definitions of the disclosure; and m1-6 are independently selected from an integer of 0 to 100, specifically like an integer of 0 to 20 and especially an integer of 0 to 12; in an example of the disclosure, all the m1-6 are 3.

Specifically, for the formula XIV, in the $A_1$, the $A_2$, the $D_1$, the $D_2$ and the B, the X is selected from one or a combination of several of —$(CH_2)_i$—, —$CO(CH_2)_i$—, —$(CH_2)_iNH$— and $(CH_2)_iCONH$—, and more specifically —$(CH_2)_i$—; specifically, i in the linking group X is 0, 1, 2, 3 or 4; and in an example of the disclosure, the X is a single bond, —$CH_2$—, —$CH_2CH_2$— or —$CH_2CH_2CH_2$—.

Specifically, for the formula XIV, in the $A_1$, the $A_2$, the $D_1$, the $D_2$ and the B, Y is selected from one of methoxy, hydroxyl, amino, azido, sulfydryl, carboxyl, ester, aldehyde group, acrylic group and maleimide group.

More specifically, in the formula XIV, the $A_1$, the $A_2$, the $D_1$ and the $D_2$ are independently selected from one of —H, —$CH_3$, —$OCH_3$, —OH, —$NH_2$, —$CH_2NH_2$, —$CH_2CH_2NH_2$, —$N_3$, —$CH_2N_3$, —$CH_2CH_2N_3$, —$CH_2COOH$, —$CH_2CH_2COOH$, —SH, —$CH_2CH_2CHO$ and —$CH_2CH_2CH_2CHO$; further specifically, the $A_1$, the $A_2$, the $D_1$ and the $D_2$ are independently selected from one of —$CH_3$, —$OCH_3$, —$CH_2CH_2NH_2$, —$CH_2CH_2COOH$ and —$CH_2CH_2N_3$; and in an example of the disclosure, the $A_1$, the $A_2$, the $D_1$ and the $D_2$ are all —$CH_2CH_2NH_2$.

More specifically, in the formula XIV, the B is selected from one of —H, —OH, —$NH_2$, —$CH_2COOH$, —$CH_2CH_2COOH$, —SH, —$CH_2CH_2CHO$ and —$CH_2CH_2CH_2CHO$; and in an example of the disclosure, the B is —OH.

Specifically, in the formula XIV, the $R_{a1}$, the $R_{b1}$ and the $R_{d1}$ are —$(CH_2)_r$—, which are the same or different, and r is selected from an integer of 0 to 10, and more specifically, the $R_{a1}$, the $R_{b1}$ and the $R_{d1}$ are —$(CH_2)_r$—, which are the same or different, and r is selected from an integer of 0 to 5; and in an example of the disclosure, the $R_{a1}$ and the $R_{d1}$ are both —$C_2H_4$—, and the $R_{b1}$ is-$C_3H_6$—.

More specifically, in the formula XIV, the —$R_{b1}$—B is —$C_3H_6$—OH.

In an example of the disclosure, the dendritic polyethylene glycol derivative has a structure as follows:

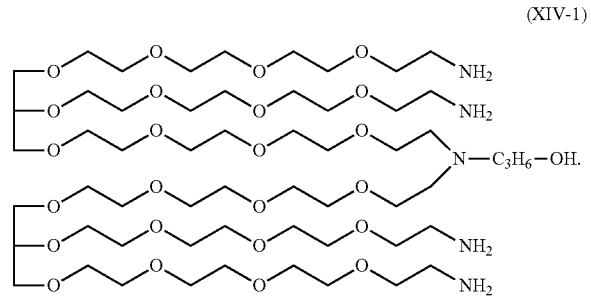

(XIV-1)

In a specific example of the disclosure, the dendritic polyethylene glycol derivative has a structure as follows:

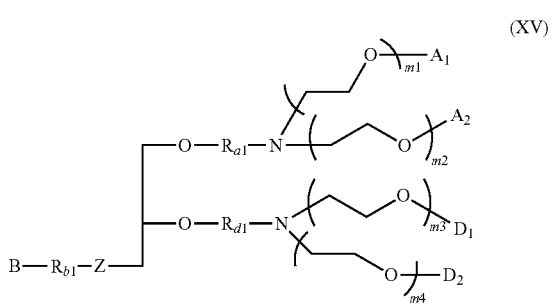

(XV)

wherein, the $R_{a1}$, the $R_{b1}$, the $R_{d1}$, the $A_1$, the $A_2$, the $D_1$, the $D_2$, the B and the Z have the above definitions of the disclosure;

m1-4 are independently selected from an integer of 0 to 100, specifically like an integer of 0 to 20 and especially an integer of 0 to 12; and in an example of the disclosure, all the m1-4 are 4.

Specifically, in the formula XV, in the $A_1$, the $A_2$, the $D_1$, the $D_2$ and the B, the X is selected from one or a combination of several of —$(CH_2)_i$—, —$CO(CH_2)_i$—, —$(CH_2)_iNH$— and $(CH_2)_iCONH$—, and more specifically —$(CH_2)_i$—; specifically, i in the linking group X is 0, 1, 2, 3 or 4; and in an example of the disclosure, the X is a single bond, —$CH_2$—, —$CH_2CH_2$— or —$CH_2CH_2CH_2$—.

Specifically, in the formula XV, in the $A_1$, the $A_2$, the $D_1$, the $D_2$ and the B, the Y is selected from one of methoxy, hydroxyl, amino, azido, sulfydryl, carboxyl, ester, aldehyde group, acrylic group and maleimide group.

More specifically, in the formula XV, the $A_1$, the $A_2$, the $D_1$ and the $D_2$ are independently selected from one of —H, —$CH_3$, —$OCH_3$, —OH, —$NH_2$, —$CH_2NH_2$, —$CH_2CH_2NH_2$, —$N_3$, —$CH_2N_3$, —$CH_2CH_2N_3$, —$CH_2COOH$, —$CH_2CH_2COOH$, —SH, —$CH_2CH_2CHO$ and —$CH_2CH_2CH_2CHO$; more specifically, the $A_1$, the $A_2$, the $D_1$ and the $D_2$ are independently selected from one of —$CH_3$, —$OCH_3$, —$CH_2CH_2NH_2$—, —$CH_2CH_2CHO$ and —$CH_2CH_2N_3$; and in an example of the disclosure, the $A_1$, the $A_2$, the $D_1$ and the $D_2$ are all —$CH_3$ or —$CH_2CH_2COOH$;

More specifically, in the formula XV, the B is selected from one of —H, —OH, —$NH_2$, —$CH_2COOH$, —$CH_2CH_2COOH$, —SH, —$CH_2CH_2CHO$ and —$CH_2CH_2CH_2CHO$; in an example of the disclosure, the B is —H.

Specifically, in the formula XV, the $R_{a1}$, the $R_{b1}$ and the $R_{d1}$ are —$(CH_2)_r$—, which are the same or different, and r is selected from an integer of 0 to 10, and more specifically, the $R_{a1}$, the $R_{b1}$ and the $R_{d1}$ are —$(CH_2)_r$—, which are the same or different, and r is selected from an integer of 0 to 5; and in an example of the disclosure, the $R_{a1}$ and the $R_{d1}$ are both —$C_2H_4$—, and the $R_{b1}$ is a single bond.

Specifically, in the formula XV, the Z is O or NHCO.

More specifically, in the formula XV, the —Z—$R_{b1}$—B is —OH.

In an example of the disclosure, the dendritic polyethylene glycol derivative has a structure as follows:

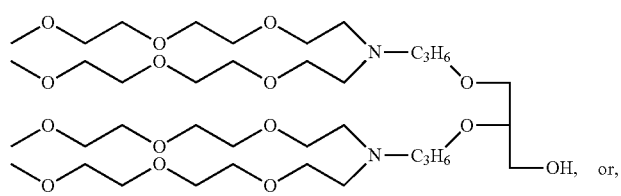

(XV-1)

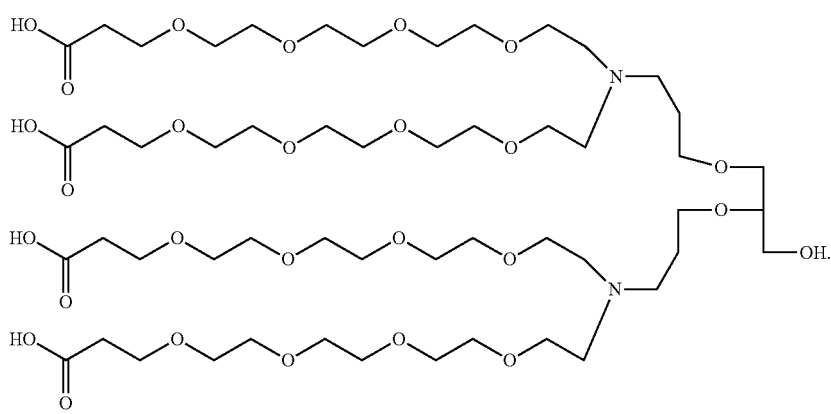

(XV-2)

In a specific example of the disclosure, the dendritic polyethylene glycol derivative has a structure as follows:

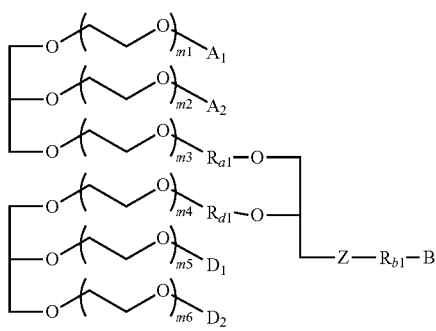

(XVI)

wherein, the $R_{a1}$, the $R_{b1}$, the $R_{d1}$, the $A_1$, the $A_2$, the $D_1$, the $D_2$, the B and the Z have the above definitions of the disclosure;

m1-6 are independently selected from an integer of 0 to 100, for example, an integer of 0 to 20, and especially an integer of 0 to 12; and in an example of the disclosure, all the m1-6 are 3.

Specifically, in the formula XVI, in the $A_1$, the $A_2$, the $D_1$, the $D_2$ and the B, the X is selected from one or a combination of several of —(CH$_2$)$_i$—, —CO(CH$_2$)$_i$—, —(CH$_2$)$_i$NH— and (CH$_2$)$_i$CONH—, and more specifically —(CH$_2$)$_i$—; specifically, i in the linking group X is 0, 1, 2, 3 or 4; and in an example of the disclosure, the X is a single bond, —CH$_2$—, —CH$_2$CH$_2$— or —CH$_2$CH$_2$CH$_2$—.

Specifically, in the formula XVI, in the $A_1$, the $A_2$, the $D_1$, the $D_2$ and the B, the Y is selected from one of methoxy, hydroxyl, amino, azido, sulfydryl, carboxyl, ester, aldehyde group, acrylic group and maleimide group.

More specifically, in the formula XVI, the $A_1$, the $A_2$, the $D_1$ and the $D_2$ are independently selected from one of —H, —CH$_3$, —OCH$_3$, —OH, —NH$_2$, —CH$_2$NH$_2$, —CH$_2$CH$_2$NH$_2$, —N$_3$, —CH$_2$N$_3$, —CH$_2$CH$_2$N$_3$, —CH$_2$COOH, —CH$_2$CH$_2$COOH, —SH, —CH$_2$CH$_2$CHO and —CH$_2$CH$_2$CH$_2$CHO; more specifically, the $A_1$, the $A_2$, the $D_1$ and the $D_2$ are independently selected from one of —CH$_3$, —OCH$_3$, —CH$_2$CH$_2$NH$_2$, —CH$_2$CH$_2$COOH and —CH$_2$CH$_2$N$_3$; and in an example of the disclosure, the $A_1$, the $A_2$, the $D_1$ and the $D_2$ are all —CH$_3$ or —CH$_2$CH$_2$NH$_2$.

More specifically, in the formula XVI, the B is selected from one of —H, —OH, —NH$_2$, —CH$_2$COOH, —CH$_2$CH$_2$COOH, —SH, —CH$_2$CH$_2$CHO and —CH$_2$CH$_2$CH$_2$CHO, and further specifically, is —H or —CH$_2$CH$_2$COOH.

Specifically, in the formula XVI, the $R_{a1}$, the $R_{b1}$ and the $R_{d1}$ are —(CH$_2$)$_r$—, which are the same or different, and r is selected from an integer of 0 to 10, and more specifically, the $R_{a1}$, the $R_{b1}$ and the $R_{d1}$ are —(CH$_2$)$_r$—, which are the same or different, and r is selected from an integer of 0 to 5; and in an example of the disclosure, the $R_{a1}$ and the $R_{d1}$ are both —C$_2$H$_4$—, and the $R_{b1}$ is a single bond.

Specifically, in the formula XVI, the Z is O or NHCO.

More specifically, in the formula XVI, the —Z—$R_{b1}$—B is —OH or —NHCO—CH$_2$CH$_2$COOH.

In an example of the disclosure, the dendritic polyethylene glycol derivative has a structure as follows:

(XVI-1)

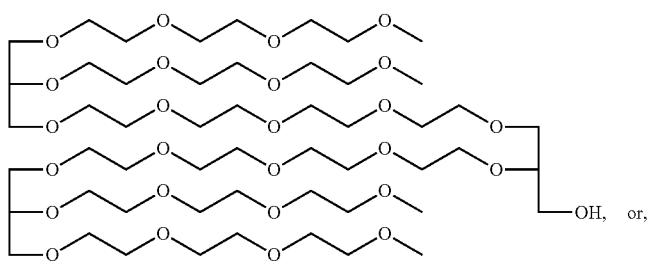

OH, or, (XVI-2)

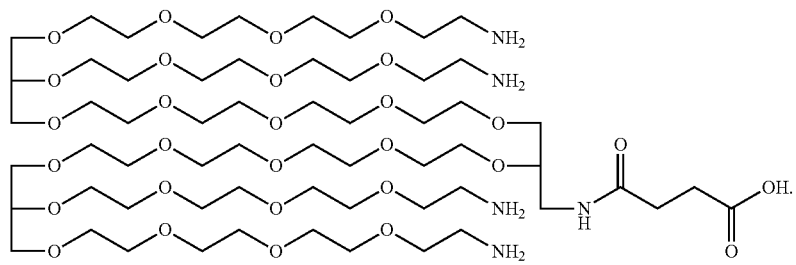

The disclosure further provides a preparation method of the above dendritic polyethylene glycol derivative employing a convergent synthesis method, including the following steps of:

(1) modifying one end of a polyethylene glycol derivative, and then linking the modified end with a central molecule through nucleophilic substitution reaction or amidation reaction to obtain a wedge-shaped structure; and (2) modifying one end group at the central molecule part of the compound obtained through step (1), and then linking the modified end with another molecule central molecule through nucleophilic substitution reaction or amidation reaction to obtain a four-arm dendritic polyethylene glycol derivative;

wherein dendritic polyethylene glycol derivatives with exponentially increased number of arms such as eight-arm and sixteen-arm can be obtained by analogy;

the polyethylene glycol derivative in the step (1) has a structure of R—X-E-$R_t$—OH, R—X-E-$R_t$—$NH_2$ or R—X-E-$R_t$—COOH;

wherein, $R_t$ is selected from one or a combination of several of —$(CH_2)_t$—, —$(CR_1R_2)_t$—, —$(CH_2)_tNH$—, —NHCO$(CH_2)_t$—, —$(CH_2)_tCONH$— and —CO$(CH_2)_t$—, and t is an integer of 0 to 30;

$R_1$ and $R_2$ are independently selected from one or a combination of several of —H, C1-C6 alkyl, —OR', —NHR', —N(R')$_2$, —CN, —F, —Cl, —Br, —I, —COR', —COOR', —OCOR', —CONHR' and —CON(R')$_2$, R" is selected from —H, C1-C6 alkyl, —F, —Cl, —Br and —I, X is a linking group selected from one or a combination of more than two of —$(CH_2)_i$—, —$(CH_2)_iNH$—, —CO$(CH_2)_i$—, —$(CH_2)_iOCOO$—, —$(CH_2)_iOCONH$—, —$(CH_2)_iNHCONH$—, —OC$(CH_2)_iCOO$—, —$(CH_2)_iCOO$— and —$(CH_2)_iCONH$—, and i is an integer of 0 to 10;

R is an active end group defined by the Y in the structure of formula (I) or R is selected from one of the following groups: methyl ester, ethyl ester, tert-butyl ester, acetal group, benzyloxy, tert-butoxy, imino and halogen;

Y is an end group selected from one of C1-C6 alkyl, C1-C6 alkoxy, H (hydrogen atom), hydroxyl, amino, aminomethyl, maleimide, carboxyl, ester, sulfydryl, succinimidyl carbonate, succinimidyl acetate, succinimidyl propionate, succinimidyl succinate, succinimidyl, dithiopyridyl, propionic acid, aldehyde group, thioester group, acrylic group, acryloxy, azido, glutaric group, hydrazide, alkynyl, p-nitrophenyl carbonate, isocyanato, silane group, carboxymethyl, vinyl sulfone group and vitamin H residue;

E is a polyethylene glycol group with a structure of (OCH$_2$CH$_2$)$_m$, and m is an integer of 0 to 100;

the modified group is selected from one of

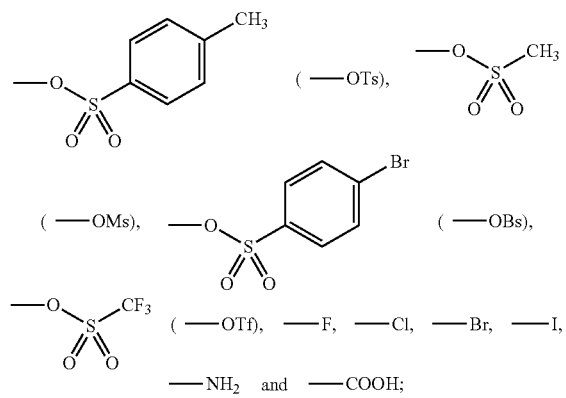

the central molecule is a compound containing amino and/or hydroxyl and/or carboxyl, and preferably, the compound contains following structures: —NH$_2$,

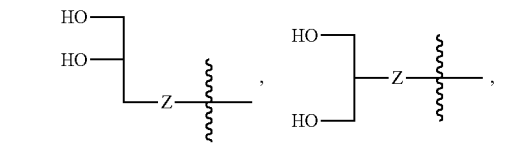

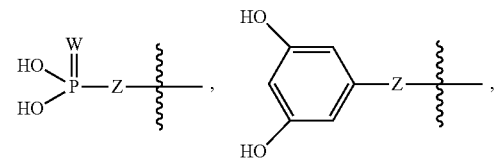

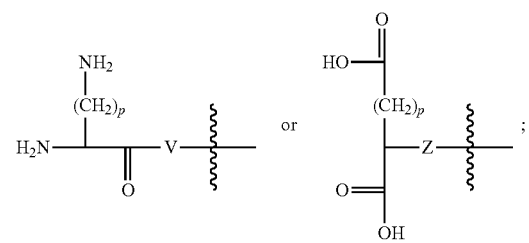

Z is selected from one of O, S, NH, NHCO, CO, COO, OC(O) and $(CH_2)_s$, and s is an integer of 0 to 10;

p is an integer of 0 to 10;

W is O or S; and

V is O or NH.

Specifically, the $R_t$ is $—(CH_2)_t—$.

Specifically, the t is an integer of 0 to 10, for example, 0, 1, 2, 3, 4 or 5.

Specifically, the X is selected from one or a combination of several of $—(CH_2)_i—$, $—CO(CH_2)_i—$, $—(CH_2)_iNH—$ and $(CH_2)_iCONH—$; and is preferably $—(CH_2)_i$.

Specifically, i in the linking group X is 0, 1, 2, 3 or 4.

Specifically, the R is selected from one of methyl ester, ethyl ester, tert-butyl ester, azido, acetal group and benzyloxy.

Specifically, the m is an integer of 0 to 20, for example, an integer of 0 to 12; and specifically, the m is 0, 1, 2, 3, 4, 5, 6, 7 or 8.

Specifically, the Z is selected from one of O, NH, NHCO and $(CH_2)_s$, and more specifically, O or NHCO.

Specifically, the s is 0, 1, 2, 3, 4 or 5.

Specifically, the p is 0, 1, 2, 3, 4 or 5.

In a preferred example of the disclosure, the central molecule following structures:

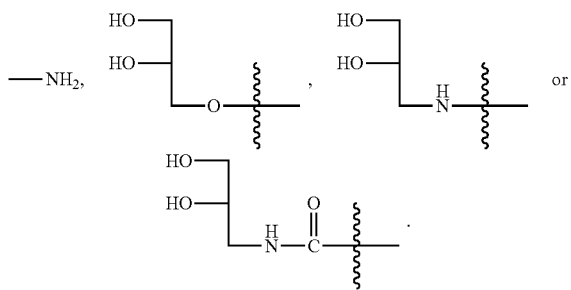

Specifically, one end of the central molecule part of the reaction product obtained in the step (1) and/or step (2) can be linked with the polyethylene glycol modified by a leaving group through nucleophilic substitution reaction.

The step of modifying the ionic groups and the step of nucleophilic substitution reaction with the central molecule in the above preparation method can be carried out by the method disclosed in the prior art, and the disclosure is not specifically limited to this.

Those skilled in the art may modify and transform the end groups of the dendritic polyethylene glycol derivative prepared above according to actual application requirements, and may also modify and transform the corresponding end groups in the preparation process. Synthesis methods disclosed in the prior art, such as carboxylation and subsequent succinimidation, amination, aldehyde-forming, thiolation, maleimidation, acrylation, and the like, may be used as method for modifying and transforming the end groups, and the disclosure is not specifically limited to this.

The disclosure further provides an application of the above dendritic polyethylene glycol derivative in fields of supramolecular chemistry, biomedicine, photochemistry, or electrochemistry, or catalyst.

In an example of the disclosure, the application is an application of the dendritic polyethylene glycol derivative in biomedicine.

Specifically, the application is an application of the above dendritic polyethylene glycol derivative in a modified drug; and more specifically, the drug is an insoluble drug.

The disclosure further provides a covalent conjugate, including the above dendritic polyethylene glycol derivative and a drug molecule linked by a covalent bond.

Specifically, the drug is an insoluble drug.

In an example of the disclosure, the drug is cholesterol, hexadecanol or menthol.

The disclosure further provides an application of the above dendritic polyethylene glycol derivative in preparing the above covalent conjugate.

The insoluble drugs in the disclosure are sparingly soluble, slightly soluble and very slightly soluble drugs according to the detection method of the Chinese Pharmacopoeia.

The dendritic polyethylene glycol derivative provided by the disclosure has a plurality of end functional groups, has a stronger water solubility in comparison with a linear-chain polyethylene glycol, and can solve a problem of insufficient water solubility due to the increase of load when modifying the insoluble drug by the polyethylene glycol. The preparation method of the dendritic polyethylene glycol derivative provided by the disclosure has mild reaction conditions, is green and environmentally friendly, is low in cost, and is easy to implement industrialization.

DETAILED DESCRIPTION OF THE EMBODIMENTS

Figure 1:
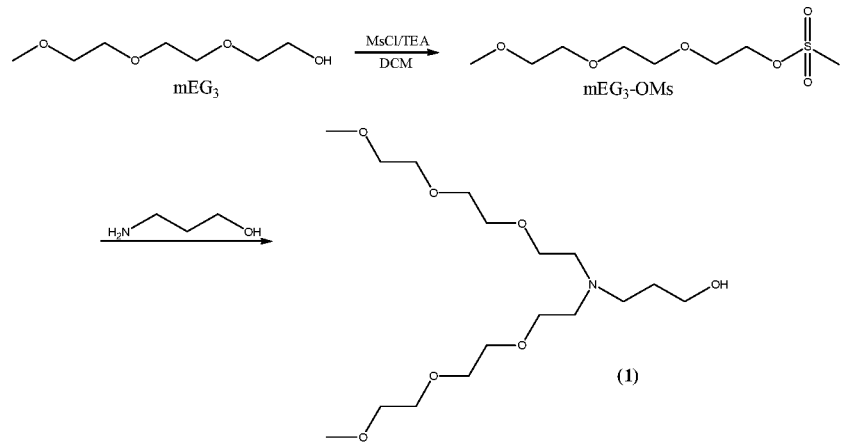
FIG. 1 is a diagram illustrating a synthetic route of $(mEG_3)_2N—C_3H_6—OH$ (1).

Unless otherwise defined, all the technical and scientific terms used in the disclosure have the same meaning as commonly understood by those skilled in the art to which the disclosure belongs. For example, "alkyl" refers to linear-chain or branched-chain hydrocarbon chain radical without unsaturated bonds, and C1-C6 alkyl refers to alkyl containing 1 to 6 carbon atoms, such as methyl, ethyl, n-propyl, isopropyl, n-butyl, isobutyl, tert-butyl, n-pentyl, n-hexyl, or the like; "alkoxy" refers to a substituent formed after hydrogen in hydroxyl is substituted by alkyl, and C1-C6 alkoxy refers to alkoxy containing 1 to 6 carbon atoms, such as methoxy, ethoxy, propoxy, butoxy, or the like. In addition, some groups involved in the disclosure and chemical structures thereof correspond to the followings: hydroxyl, —OH; amino, —$NH_2$; aminomethyl-$CH_2NH_2$; maleimide group,

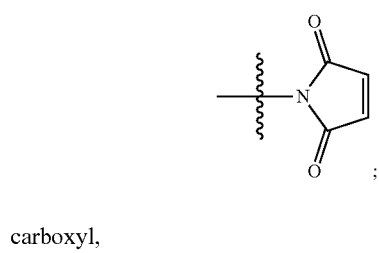

carboxyl,

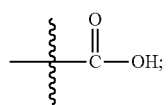 [SMILES: *C(=O)O]

ester,

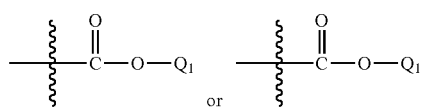

(wherein $Q_1$ may be an alkyl, an aryl or a heterocyclyl, such as a methyl, an ethyl, an n-propyl, a t-butyl,

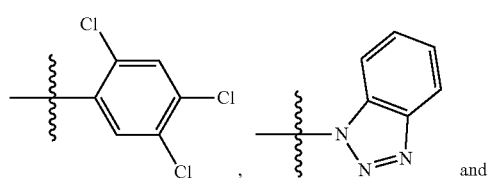

etc.); sulfydryl, —SH; succinimidyl carbonate group,

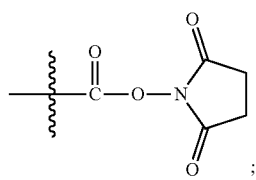 [SMILES: *C(=O)ON1C(=O)CCC1=O]

succinimidyl acetate group,

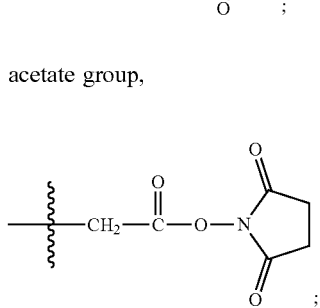

succinimidyl propionate group,

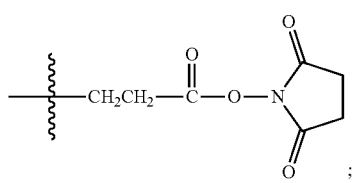

a succinimidyl succinate group,

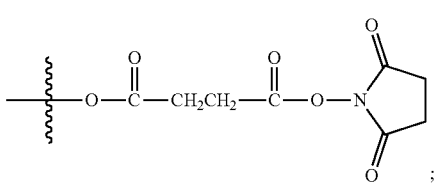

succinimidyl,

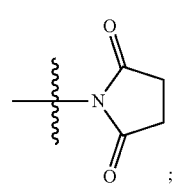 [SMILES: *N1C(=O)CCC1=O]

dithiopyridyl, such as 2-pyridyldithio

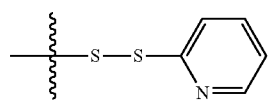

and 4-pyridyldithio,

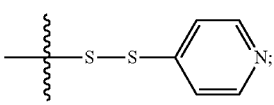 [SMILES: *SSc1ccncc1]

propionic acid,

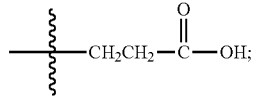

aldehyde group, —CHO; thioester

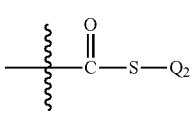

(wherein $Q_2$ may be alkyl, such as methyl, ethyl, n-propyl, tert-butyl, etc.); acrylic group, acryloxy

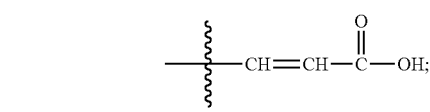 [SMILES: *C=CC(=O)O]

azido,

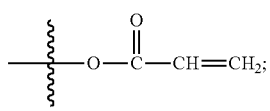

glutaric group, such as

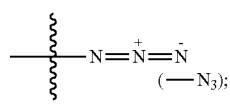

hydrazide,

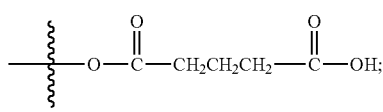

alkynyl,

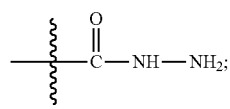

p-nitrophenyl carbonate,

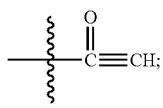

isocyanato,

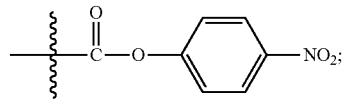 [SMILES: *C(=O)Oc1ccc([N+](=O)[O-])cc1]

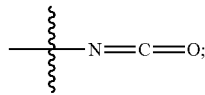 [SMILES: *N=C=O]

silane group,

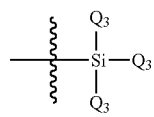

(wherein $Q_3$ may be alkyl or alkoxy, which may be the same or different, such as methyl, ethyl, propyl, butyl, pentyl, methoxy, ethoxy, propoxy, butoxy, or the like; and preferably, all the $Q_3$ are methyl, ethyl, n-propyl, methoxy, ethoxy, n-propoxy, etc.); carboxymethyl,

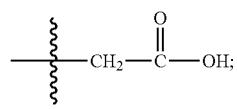

vinylsulphone group,

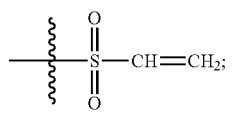 [SMILES: *S(=O)(=O)C=C]

and vitamin H residue,

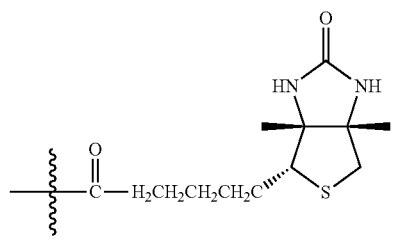

The convergent synthesis method described in the disclosure refers to starting from an edge part of a dendrimer molecule to be synthesized, and proceeding inwards gradually. First, a part of a dendritic macromolecule, i.e., a wedge-shaped structure, is synthesized by using a divergent method, and then the synthesized part of the dendritic macromolecule is linked with a core to finally form the dendrimer (as described in "19(3): 6-9 of Fine and Specialty Chemicals, Synthesis and Application of Dendrimer [J], 2011", written by Wang Hetong).

The following clearly and completely describes the technical solutions of the disclosure with reference to the examples of the disclosure. Apparently, the described examples are merely some but not all of the examples of the disclosure. Based on the examples in the disclosure, all other examples obtained by those of ordinary skills in the art without going through any creative work shall fall within the scope of protection of the disclosure.

Example 1 Synthesis of Raw Materials

I. Synthesis of Raw Material $(mEG_3)_2N$—$C_3H_6$—OH(1)

A synthetic route of the $(mEG_3)_2N$—$C_3H_6$—OH(1) is as shown in FIG. 1.

1. Synthesis of $mEG_3$-OMs

TEA (32 mL, 230 mmol) and 150 mL of DCM were added to $mEG_3$-OH (32 mL, 200 mmol) and placed in a reaction flask in an ice-water bath. MsCl (17.5 mL, 220 mmol) was dissolved with DCM (50 mL) and added dropwise to the reaction flask in the ice-water bath after the MsCl was completely dissolved. The mixture was reacted at room temperature for 3 hours. The reaction was detected to be complete by a thin layer chromatography (TLC). The resulting product was washed with water (150 mL) three times. An organic phase was dried with anhydrous sodium sulfate and filtered to remove sodium sulfate. The remaining was concentrated to obtain about 52 g of product.

2. Synthesis of $(mEG_3)_2N$—$C_3H_6$—OH

The $mEG_3$-OMs (21.6 g, 89.3 mmol) prepared in the step 1 above and THF (150 mL) were added to aminopropanol (3.1 g, 41.3 mmol). After heating and refluxing overnight, a supernatant was poured out and evaporated to dryness to obtain a crude product. The crude product was subjected to column purification (250 g of silica gel, a MeOH/DCM system being a mobile phase, MeOH/DCM=3-7%) to obtain 2.5 g of product with a yield of 16%.
NMR(CDCl$_3$) δ: 3.5-3.8 (m, 22H, OCH$_2$), 3.37 (s, 6H, CH$_3$O), 2.7-2.8 (m, 6H, N(CH$_2$)$_3$), 1.6-1.7 (m, 2H, NCH$_2$CH$_2$CH$_2$OH); ESI-MS: 368.3 (M+H)$^+$, 390.2 (M+Na)$^+$.

II. Synthesis of Raw Material $(mEG_3)_2$-OH

Figure 2:
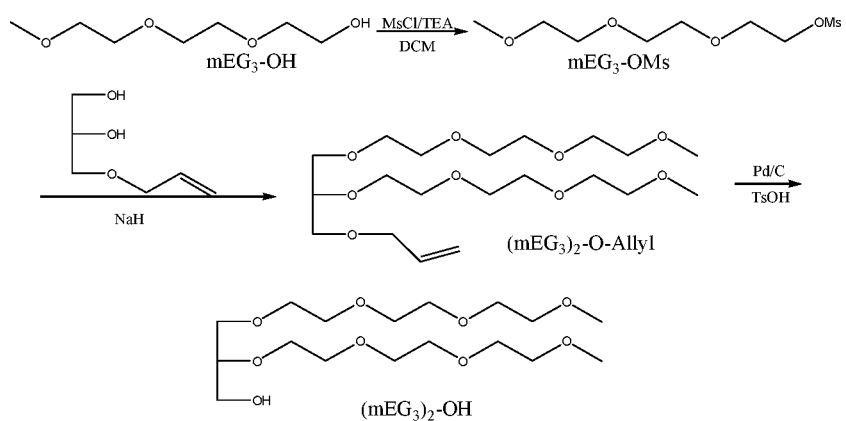
FIG. 2 is a diagram illustrating a synthetic route of $(mEG_3)_2$-OH.

A synthetic route of the $(mEG_3)_2$-OH is as shown in FIG. 2.

1. Synthesis of $mEG_3$-OMs

TEA (32 mL, 230 mmol) and DCM (150 mL) were added to $mEG_3$-OH (32 mL, 200 mmol) and placed in a reaction flask in an ice-water bath. MsCl (17.5 mL, 220 mmol) was dissolved with DCM (50 mL) and added dropwise to the reaction flask in the ice-water bath after the MsCl was completely dissolved. The mixture was reacted at room temperature for 3 hours. The reaction was detected to be complete by a thin layer chromatography (TLC). The remaining was washed with water (150 mL) three times. An organic phase was dried with anhydrous sodium sulfate and filtered to remove sodium sulfate. The remaining was concentrated to obtain about 52 g of product.

2. Synthesis of $(mEG_3)_2$-O-Allyl

Toluene (75 mL) was added to 3-propenyloxy-1,2-propanediol (3.01 mL), then NaH (60%, 2.05 g) was added under an ice-water bath and reacted at room temperature for 2 hours; a toluene solution (80 mL) containing $mEG_3$-OMs was added dropwise, and reacted at 60° C. overnight; then HPLC detection was carried out, and the toluene was evaporated to dryness; the remaining was added with DCM and water and washed once respectively, and then the DCM was evaporated to dryness to obtain a crude product. The crude product was subjected to column purification (1% MeOH/DCM being a mobile phase) to obtain 8.8 g of product (with a yield of 85%).

3. Synthesis of $(mEG_3)_2$-OH

Pd/C (0.8 g) and TsOH (1.6 g) were added to the product (8 g) of the step 2 above, then methanol (80 mL)/water (16 mL) was added and refluxed for 24 hours. It was found by HPLC that the reaction was complete. Pd/C was recovered by filtration and then concentrated to obtain a crude product. The crude product was subjected to column purification (3% MeOH/DCM) to obtain 5.8 g of product (with a yield of 80.2%).
NMR(CDCl$_3$) δ: 3.89-3.50 (m, 29H), 3.38 (s, 6H); ESI-MS: 385.4 (M+H)$^+$, 407.2 (M+Na)$^+$.

III. Synthesis of Raw Material $(tBuOC-EG_4)_2N$—$C_3H_6$—OH (2)

Figure 3:
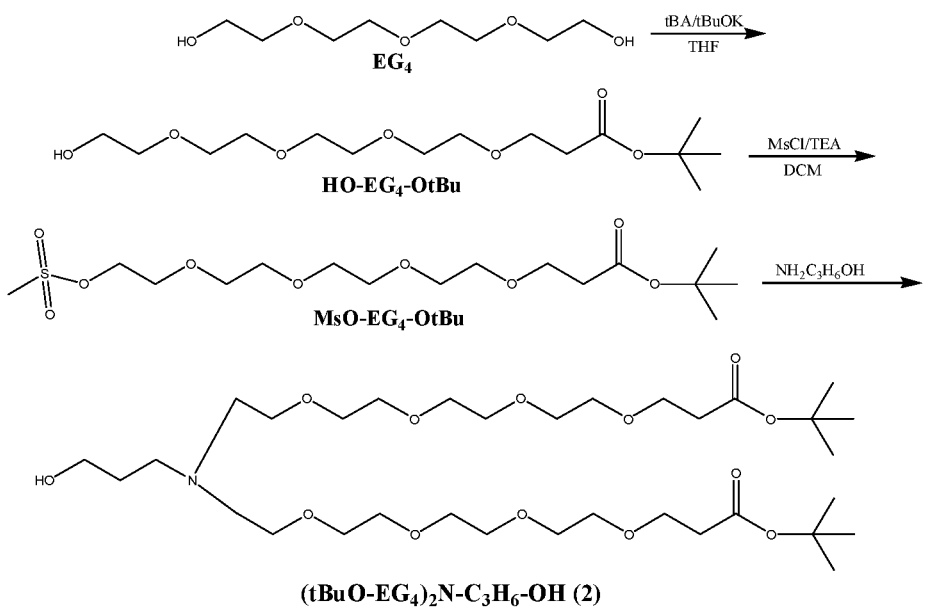
FIG. 3 is a diagram illustrating a synthetic route of $(tBuOC-EG_4)_2N—C_3H_6—OH$ (2).

A synthetic route of the $(tBuOC-EG_4)_2N$—$C_3H_6$—OH (2) is as shown in FIG. 3.

1. Synthesis of $MsO-EG_4$-OtBu

DCM (350 mL) and TEA (22.7 mL, 0.159 mol, 1.3 eq) were added to $HO-EG_4$-tBu (39.4 g, 0.122 mol). A DCM (150 mL) solution of MsCl (11.4 mL, 0.146 mol, 1.2 eq) were added under an ice-water bath, and reacted at room temperature overnight. The remaining was washed with water (200 mL) three times in turn, dried by over anhydrous sodium sulfate, filtered, and then a solvent was removed by evaporation to obtain a product.

2. Synthesis of $(tBuO-EG_4)_2N$—$C_3H_6$—OH

Aminopropanol (1.9 mL, 25 mmol) and DMF (200 mL) were added to the $MsO-EG_4$-OtBu (20 g, 50 mmol) prepared in the step 1 above, and stirred at 70° C. overnight. The remaining was concentrated to obtain a crude product. The crude product was subjected to column purification (MeOH/DCM=0-10%) to obtain 2.3 g of product with a yield of 12.0%.
NMR(CDCl$_3$) δ: 3.5-3.8 (m, 34H, OCH$_2$); 3.3 (m, 6H, N(CH$_2$)$_3$); 2.5- (t, 2H, CH$_2$COO); 1.7-1.8 (m, 2H, NCH$_2$CH$_2$CH$_2$OH); 1.4 (s, 18H, (CH$_3$)$_3$—); ESI-MS: 706.3 (M+Na)$^+$.

IV. Synthesis of Raw Material $(N_3-EG_4)_2-EG_4$-OH (3)

Figure 4:
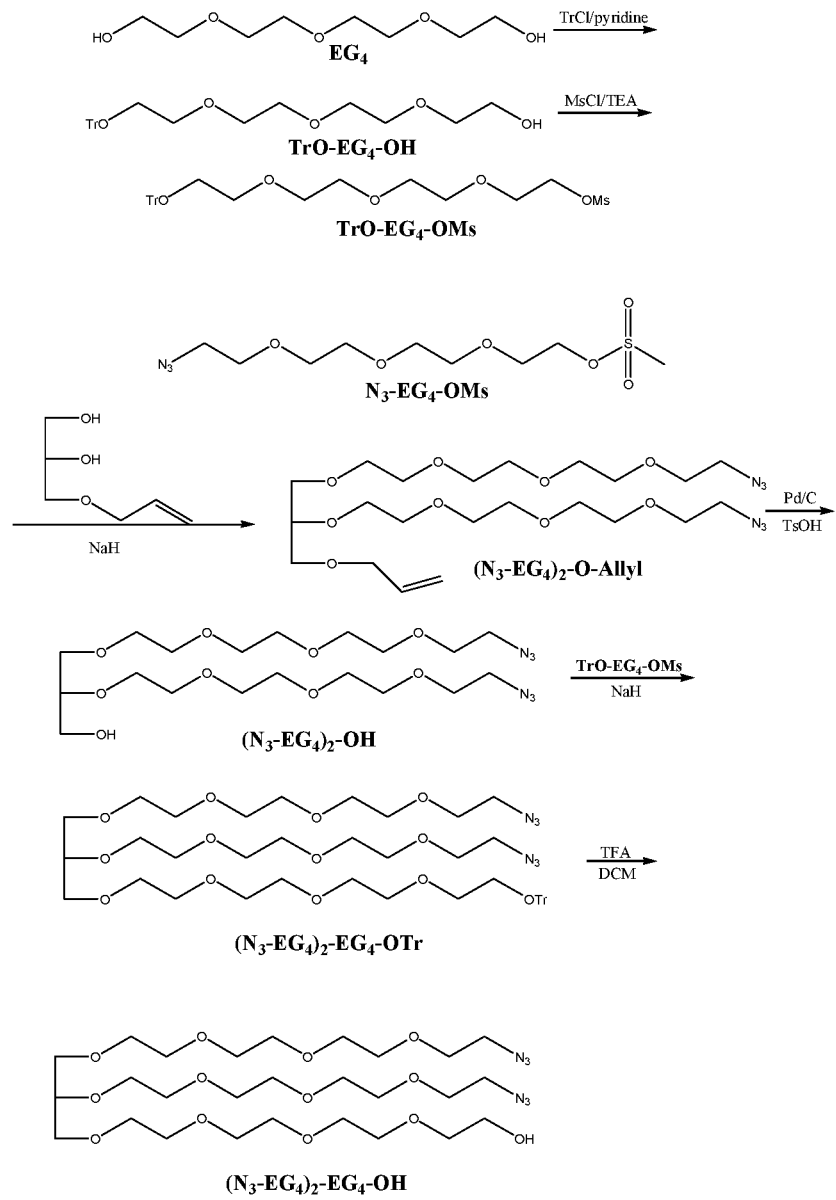
FIG. 4 is a diagram illustrating a synthetic route of $(N_3-EG_4)_2-EG_4-OH$ (3).

A synthetic route of the $(N_3-EG_4)_2-EG_4$-OH (3) is as shown in FIG. 4.

1. Synthesis of $TrO-EG_4$-OH

Toluene was added to $EG_4$ (245 g), pyridine (30 mL) was added after water was removed by azeotropy, stirred for 5 minutes, and then then triphenylchloromethane (69.7 g) was added, and stayed at room temperature overnight. The remaining was washed with water three times to obtain 87 g of product (with a yield of 80%).

2. Synthesis of $TrO-EG_4$-OMs

DCM (500 mL) and TEA (33 mL) were added to $TrO-EG_4$-OH (87 g), a DCM solution (200 mL) containing methanesulfonyl chloride (17 mL) was added dropwise under an ice-water bath, and reacted at room temperature overnight. The remaining was washed with water twice, evaporated to dryness, and then concentrated to obtain a product (with a yield of about 100%).

3. Synthesis of $(N_3-EG_4)_2$-O-Allyl

Toluene (40 mL) was added to 3-propenyloxy-1,2-propanediol (1.22 mL), then NaH (60%, 0.79 g) was added under an ice-water bath and reacted at room temperature for 2 hours; a toluene solution (80 mL) containing $N_3$-$EG_4$-OMs (6.1 g) was added dropwise, and reacted at 60° C. overnight; then HPLC detection was carried out, and the toluene was evaporated to dryness; the remaining was added with DCM and water and washed once respectively, and then the DCM was evaporated to dryness to obtain a crude product. The crude product was subjected to column purification (1% MeOH/DCM being a mobile phase) to obtain 4.3 g of product (with a yield of 85%).

4. Synthesis of $(N_3-EG_4)_2$-OH

Pd/C (0.4 g) and TsOH (0.8 g) were added to the product (4 g) of the step above, then methanol (40 mL)/water (8 mL) was added and refluxed for 24 hours. It was found by HPLC that the reaction was complete. Pd/C was recovered by filtration and then concentrated to obtain a crude product. The crude product was subjected to column purification (3% MeOH/DCM being a mobile phase) to obtain 3.0 g of product (with a yield of 82%).

5. Synthesis of $(N_3-EG_4)_2$-$EG_4$-OTr

Toluene (20 mL) was added to the product (1.5 g) of the step above, then NaH (60%, 128 mg) was added under an ice-water bath and reacted at room temperature for 2 hours; a toluene solution (10 mL) of TrO-$EG_4$-OMs (1.88 g) was added dropwise to the reaction solution, and reacted at 70° C. overnight; then the toluene was evaporated to dryness; the remaining was added with DCM and water and washed once. The DCM was evaporated to dryness to obtain a crude product. The crude product was subjected to column purification (3% MeOH/DCM being a mobile phase) to obtain 2.08 g of product (with a yield of 75.4%).

6. Synthesis of $(N_3-EG_4)_2$-$EG_4$-OH(3)

DCM (15 mL) and TFA (5 mL) were added to the product (1.5 g) of the step above, and reacted at room temperature overnight. A solvent was evaporated to dryness and saturated brine was added, the mixture was washed with ethyl ether until no color appears on a water-liquid plate, then extracted with DCM, and an organic phase was evaporated to dryness to obtain 0.69 g of product (with a yield of 62.3%).

NMR(CDCl$_3$) δ: 3.1 (m, 4H, N$_3$—CH$_2$); 3.5-3.8 (m, 50H, other hydrogen); ESI-MS: 693.2 (M+Na)$^+$.

Figure 5:
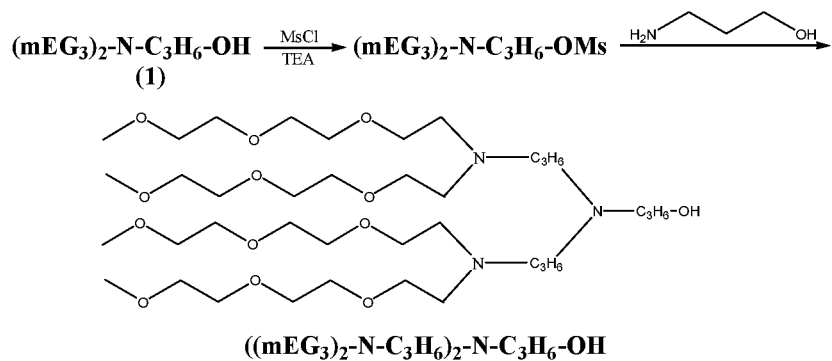
FIG. 5 is a diagram illustrating a synthetic route of a dendritic molecule $((mEG_3)_2-N—C_3H_6)_2—N—C_3H_6—OH$.

Example 2 Synthesis of Dendritic Molecule ((mEG$_3$)$_2$-N—C$_3$H$_6$)$_2$—N—C$_3$H$_6$—OH A synthetic route of the ((mEG$_3$)$_2$-N—C$_3$H$_6$)$_2$—N—C$_3$H$_6$—OH is as shown in FIG. 5.

1. Synthesis of (mEG$_3$)$_2$-N—C$_3$H$_6$-OMs

TEA (1.4 mL) and 30 mL of DCM were added to (mEG$_3$)$_2$-N—C$_3$H$_6$—OH((1), prepared in Example 1, 3.1 g), and placed in a reaction flask in an ice-water bath. MsCl (0.72 mL) was dissolved with DCM (5 mL) and added dropwise to the reaction flask in the ice-water bath after the MsCl was completely dissolved. The mixture was reacted at room temperature for 3 hours. The remaining was washed with water (30 mL) once. An organic phase was dried with anhydrous sodium sulfate and filtered to remove sodium sulfate. The remaining was concentrated to obtain about 3 g of product (with a yield of 79.8%).

2. Synthesis of Dendritic Molecule ((mEG$_3$)$_2$-N—C$_3$H$_6$)$_2$—N—C$_3$H$_6$—OH The (mEG$_3$)$_2$-N-C3H6-OMs (2.5 g) prepared in the step above and THF (30 mL) were added to aminopropanol (0.18 g). After heating and refluxing overnight, a supernatant was poured out and evaporated to dryness to obtain a crude product. The crude product was subjected to column purification (a MeOH/DCM system being a mobile phase, MeOH/DCM=3-7%) to obtain 0.4 g of product (with a yield of 20%).

NMR(CDCl$_3$) δ: 3.5-3.8 (m, 42H, OCH$_2$), 3.37 (s, 12H, CH$_3$O), 2.7-2.8 (m, 18H, N(CH$_2$)$_3$), 1.6-1.7 (m, 6H, NCH$_2$CH$_2$CH$_2$); ESI-MS: 796.5 (M+Na)$^+$.

Example 3 Synthesis of Dendritic Molecule ((mEG$_3$)$_2$-N—C$_3$H$_6$)$_2$—OH

Figure 6:
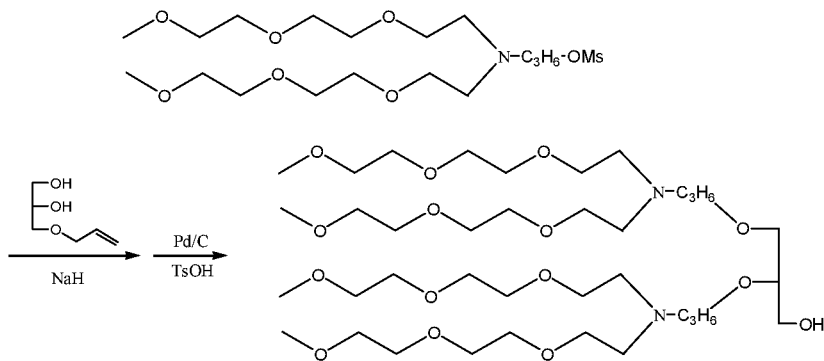
FIG. 6 is a diagram illustrating a synthetic route of a dendritic molecule $((mEG_3)_2-N—C_3H_6)_2—OH$.

A synthetic route of the ((mEG$_3$)$_2$-N—C$_3$H$_6$)$_2$—OH is as shown in FIG. 6.

Toluene (20 mL) was added to 3-propenyloxy-1,2-propanediol (0.52 g, 4 mmol), then NaH (60%, 0.5 g) was added under an ice-water bath and reacted at room temperature for 2 hours; a toluene solution (20 mL) containing (mEG$_3$)$_2$-N—C$_3$H$_6$-OMs (a synthesis method was referred to Example 2, 4.5 g) was added dropwise, and reacted at 60° C. overnight; then HPLC detection was carried out, and the toluene was evaporated to dryness; the remaining was added with DCM and water and washed once respectively, and then the DCM was evaporated to dryness to obtain a crude product.

Pd/C (0.5 g) and TsOH (0.1 g) were added to the crude reaction product (5 g) of the step above, then methanol (50 mL)/water (10 mL) was added and refluxed for 24 hours. Pd/C was recovered by filtration and then concentrated to obtain a crude product. The crude product was subjected to column purification (2-7% MeOH/DCM) to obtain 1.1 g of product (with a yield of 35%).

NMR(CDCl$_3$) δ: 3.4-3.8 (m, 48H, OCH$_2$), 3.37 (s, 12H, CH$_3$O), 3.25 (m, 1H, OCH), 2.5-2.7 (m, 12H, NCH$_2$), 1.6-1.7 (m, 4H, NCH$_2$CH$_2$CH$_2$); ESI-MS: 791.3 (M+H)+.

Example 4 Synthesis of Dendritic Molecule ((mEG$_3$)$_2$-EG$_4$)$_2$-OH

Figure 7:
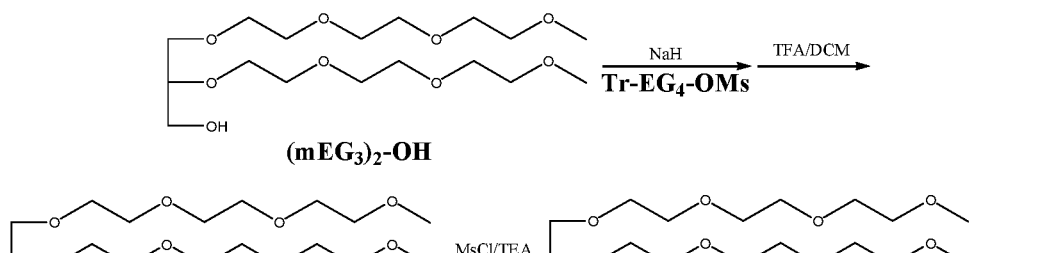
FIG. 7 is a diagram illustrating a synthetic route of a dendritic molecule $((mEG_3)_2-EG_4)_2$-OH.
Figure 7:
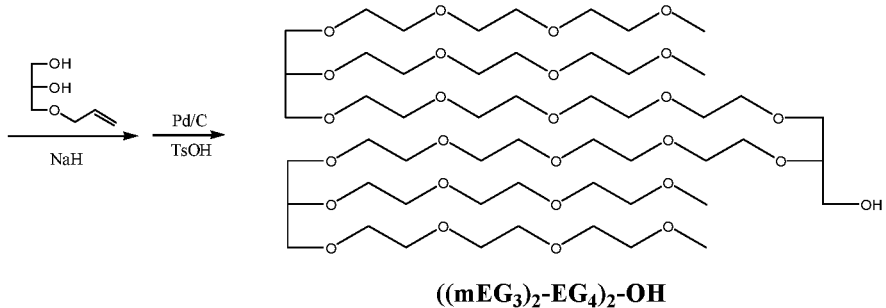

A synthetic route of the ((mEG$_3$)$_2$-EG$_4$)$_2$-OH is as shown in FIG. 7.

1. Synthesis of ((mEG$_3$)$_2$-EG$_4$)-OH

Toluene (70 mL) was added to the (mEG$_3$)$_2$-OH (synthesized in Example 1, 7.7 g), then NaH (60%, 1.0 g) was added under an ice-water bath and reacted at room temperature for 2 hours; a toluene solution (90 mL) of TrO-EG$_4$-OMs (synthesized in Example 1, 12.3 g) was added dropwise to the reaction solution, and reacted at 70° C. overnight; then the toluene was evaporated to dryness; the remaining was added with DCM and water and washed once. The DCM was evaporated to dryness to obtain a crude product. The crude product was subjected to column purification (3% MeOH/DCM being a mobile phase) to obtain 11 g of intermediate (with a yield of 69%).

DCM (100 mL) and TFA (30 mL) were added to the product (10 g) of the step above, and reacted at room temperature overnight. A solvent was evaporated to dryness and saturated brine was added, the mixture was washed with ethyl ether until no color appears on a water-liquid plate, then extracted with DCM, and an organic phase was evaporated to dryness to obtain 8.2 g of product (with a yield of 78%).

NMR(CDCl$_3$) δ: 3.89-3.50 (m, 45H), 3.38 (s, 6H); ESI-MS: 583.6 (M+Na).

2. Synthesis of ((mEG$_3$)$_2$-EG$_4$)$_2$-OMs

TEA (1.6 g) and 60 mL of DCM were added to the reaction product (7.5 g) of the above step and placed in a reaction flask in an ice-water bath. MsCl (1.76 g) was dissolved with DCM (15 mL) and added dropwise to the reaction flask in the ice-water bath after the MsCl was completely dissolved. The mixture was reacted at room temperature for 3 hours. The remaining was washed with water once. An organic phase was dried with anhydrous sodium sulfate and filtered to remove sodium sulfate. The remaining was concentrated to obtain about 8.1 g of product (with a yield of about 95%).

3. Synthesis of ((mEG$_3$)$_2$-EG$_4$)$_2$-OH

Toluene (40 mL) was added to 3-propenyloxy-1,2-propanediol (0.63 g), then NaH (60%, 0.59 g) was added under an ice-water bath and reacted at room temperature for 2 hours; a toluene solution (40 mL) containing ((mEG$_3$)$_2$-EG$_4$)$_2$-OMs (a synthesis method was referred to Example 2, 7.5 g) was added dropwise, and reacted at 60° C. overnight; then HPLC detection was carried out, and the toluene was evaporated to dryness; the remaining was added with DCM and water and washed once respectively, and then the DCM was evaporated to dryness to obtain a crude product.

Pd/C (0.8 g) and TsOH (1.6 g) were added to the crude reaction product (8 g) of the step above, then methanol (80 mL)/water (16 mL) was added and refluxed for 24 hours. Pd/C was recovered by filtration and then concentrated to obtain a crude product. The crude product was subjected to column purification (0-3% MeOH/DCM) to obtain 3.7 g of product (with a yield of 67%).

NMR(CDCl$_3$) δ: 3.89-3.50 (m, 96H), 3.35 (s, 12H); ESI-MS: 1199.2 (M+Na)$^+$.

Figure 8:
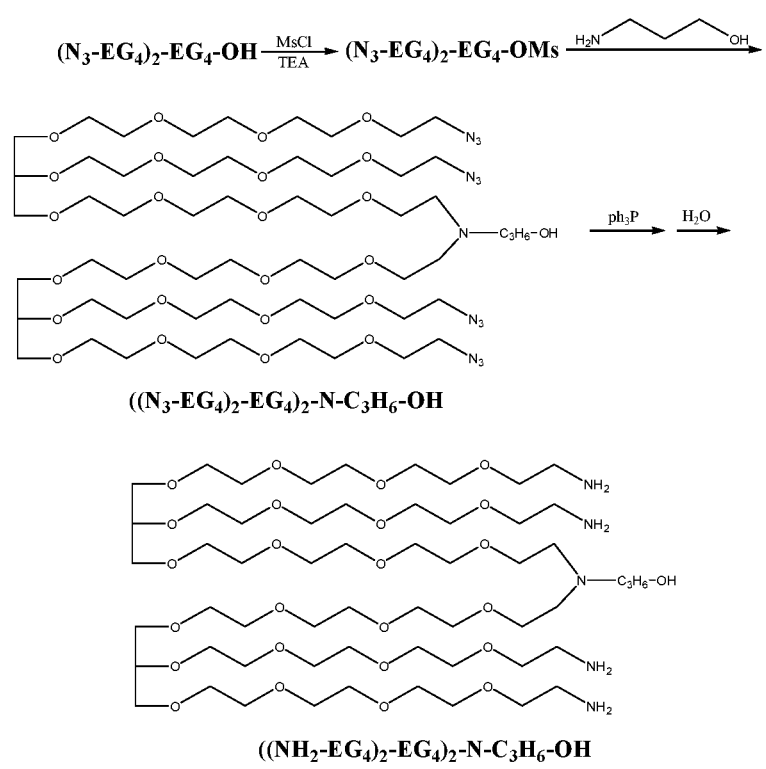
FIG. 8 is a diagram illustrating a synthetic route of a dendritic molecule $((NH_2-EG_4)_2-EG_4)_2-N—C_3H_6—OH$.

Example 5 Synthesis of Dendritic Molecule ((NH$_2$-EG$_4$)$_2$-EG$_4$)$_2$-N—C$_3$H$_6$—OH A synthetic route of the ((NH$_2$-EG$_4$)$_2$-EG$_4$)$_2$-N—C$_3$H$_6$—OH is as shown in FIG. 8.

1. Synthesis of (N$_3$-EG$_4$)$_2$-EG$_4$-OMs

TEA (1.24 mL) and 40 mL of DCM were added to (N$_3$-EG$_4$)$_2$-EG$_4$-OH ((3), prepared in Example 1, 5 g), and placed in a reaction flask in an ice-water bath. MsCl (0.63 mL) was dissolved with DCM (5 mL), and added dropwise to the reaction flask in the ice-water bath after the MsCl was completely dissolved. The mixture was reacted at room temperature for 3 hours. The remaining was washed with water (30 mL) once. An organic phase was dried with anhydrous sodium sulfate and filtered to remove sodium sulfate. The remaining was concentrated to obtain about 5.2 g of product (with a yield of 93%).

2. Synthesis of ((N$_3$-EG$_4$)$_2$-EG$_4$)$_2$-N—C$_3$H$_6$—OH (N$_3$-EG$_4$)$_2$-EG$_4$-OMs (4.5 g) prepared in the step 1 above and THF (50 mL) were added to aminopropanol (0.19 g). After heating and refluxing overnight, a supernatant was poured out and evaporated to dryness to obtain a crude product. The crude product was recrystallized by ice diethyl ether twice to obtain 0.8 g of product (with a yield of 23%).

3. Synthesis of ((NH$_2$-EG$_4$)$_2$-EG$_4$)$_2$-N—C$_3$H$_6$—OH

DMF (20 mL) and triphenylphosphine (425 mg) were added to ((N$_3$-EG$_4$)$_2$-EG$_4$)$_2$-N—C$_3$H$_6$—OH (400 mg) prepared in the step 2 above, reacted at room temperature overnight, then added with water (0.1 mL) and reacted overnight. The DMF was evaporated to dryness, then water (50 mL) was added, and the mixture was washed with ethyl acetate (40 mL) twice and DCM (30 mL) twice in sequence, then water was evaporated to dryness, and the remaining was recrystallized with ice ethyl ether twice to obtain 315 mg of product with a yield of 85%.

NMR(CDCl$_3$) δ: 1.6-1.7 (m, 2H, NCH$_2$CH$_2$CH$_2$), 2.7-2.8 (m, 14H, N(CH$_2$)$_3$&NH$_2$CH$_2$), 3.5-3.8 (m, 96H, other hydrogen excluding reactive hydrogen); ESI-MS: 1299.7 (M+Na)$^+$.

Figure 9:
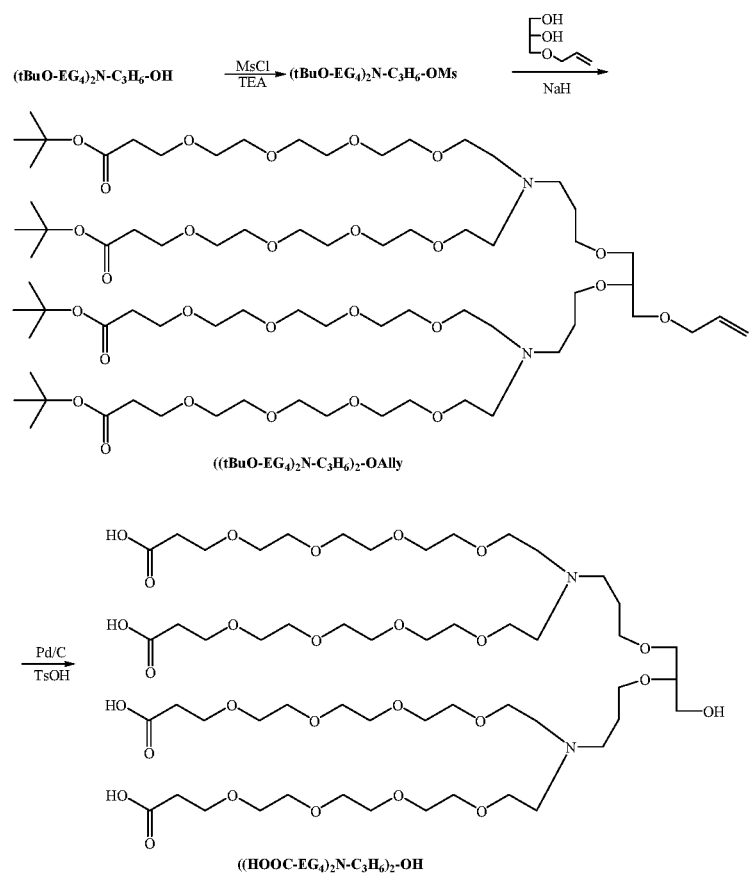
FIG. 9 is a diagram illustrating a synthetic route of a dendritic molecule $((HOOC-EG_4)_2N—C_3H_6)_2—OH$.

Example 6 Synthesis of Dendritic Molecule ((HOOC-EG$_4$)$_2$N—C$_3$H$_6$)$_2$—OH A synthetic route of the ((HOOC-EG$_4$)$_2$N—C$_3$H$_6$)$_2$—OH is as shown in FIG. 9.

1. Synthesis of (tBuO-EG$_4$)$_2$N—C$_3$H$_6$-OMs

TEA (0.54 mL) and 30 mL of DCM were added to (tBuO-EG$_4$)$_2$N—C$_3$H$_6$—OH ((2), prepared in Example 1, 2.2 g), and placed in a reaction flask in an ice-water bath. MsCl (0.27 mL) was dissolved with DCM (5 mL), and added dropwise to the reaction flask in the ice-water bath after the MsCl was completely dissolved. The mixture was reacted at room temperature for 3 hours. The remaining was washed with water (30 mL) once. An organic phase was dried with anhydrous sodium sulfate and filtered to remove sodium sulfate. The remaining was concentrated to obtain about 1.7 g of product (with a yield of 69%).

2. Synthesis of ((tBuO-EG$_4$)$_2$N—C$_3$H$_6$)$_2$-OAlly

Toluene (20 mL) was added to 3-propenyloxy-1,2-propanediol (68 mg), then NaH (60%, 72 mg) was added under an ice-water bath and reacted at room temperature for 2 hours; a toluene solution (10 mL) (tBuO-EG$_4$)$_2$N—C$_3$H$_6$-OMs (1.5 g) was added dropwise, and reacted at 60° C. overnight; then HPLC detection was carried out, and the toluene was evaporated to dryness; the remaining was recrystallized by ice diethyl ether twice to obtain 0.15 g of product (with a yield of 20%).

3. Synthesis of ((HOOC-EG$_4$)$_2$N—C$_3$H$_6$)$_2$—OH

Pd/C (0.08 g) and TsOH (0.16 g) were added to the product (0.8 g) of the step above, then methanol (10 mL)/ water (2 mL) was added and refluxed for 24 hours. It was found by HPLC that the reaction was complete. Pd/C was recovered by filtration, concentrated and then recrystallized by ice diethyl ether twice to obtain 0.56 g of product (with a yield of 86%).

NMR(CDCl$_3$) δ: 1.6-1.7 (m, 4H, NCH$_2$CH$_2$CH$_2$), 2.5-2.8 (m, 20H, N(CH$_2$)$_3$&CH$_2$COOH), 3.5-3.8 (m, 73H, other hydrogen excluding reactive hydrogen); ESI-MS: 1221.2 (M+Na)$^+$.

Figure 10:
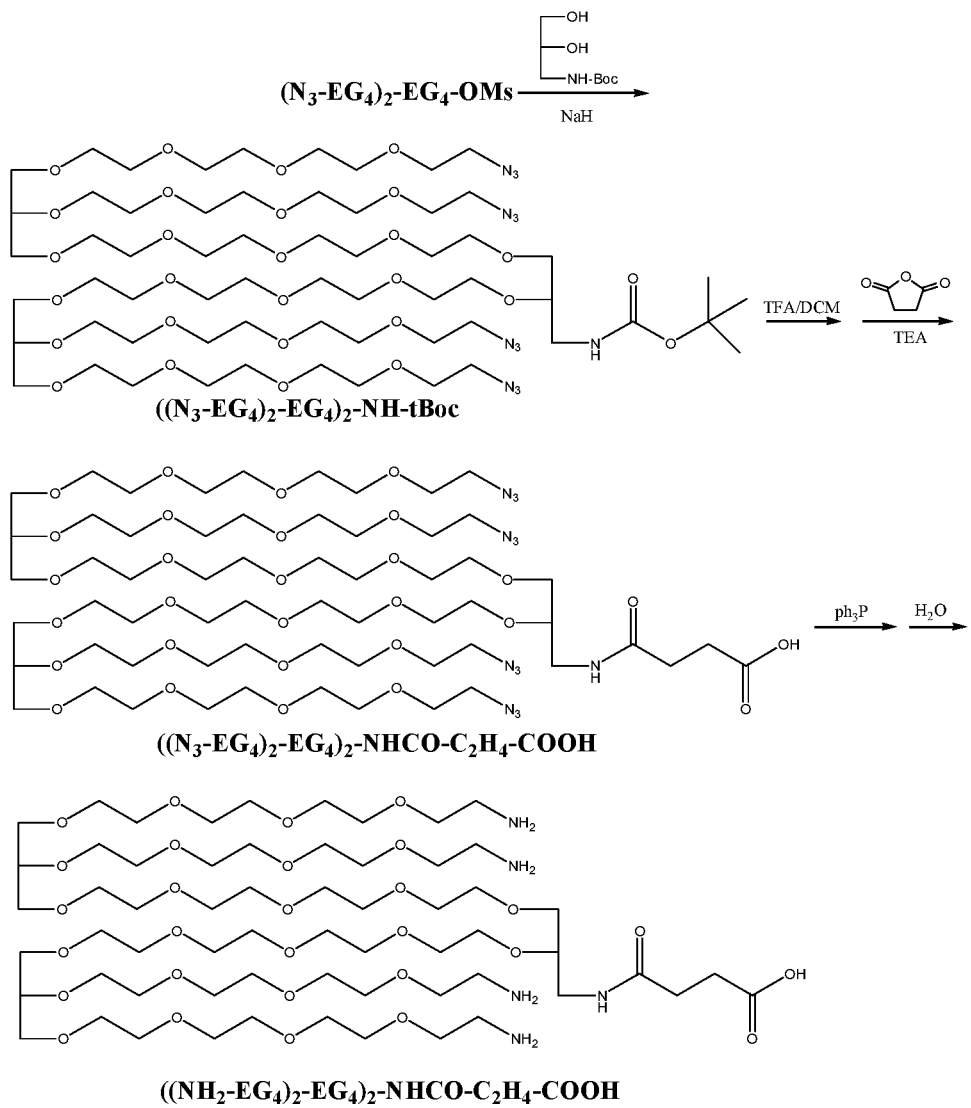
FIG. 10 is a diagram illustrating a synthetic route of a dendritic molecule $((NH_2-EG_4)_2-EG_4)_2$-NHCO—$C_2H_4$—COOH.

Example 7 Synthesis of Dendritic Molecule ((NH$_2$-EG$_4$)$_2$-EG$_4$)$_2$-NHCO—C$_2$H$_4$—COOH A synthetic route of the ((NH$_2$-EG$_4$)$_2$-EG$_4$)$_2$-NHCO—C$_2$H$_4$—COOH is as shown in FIG. 10.

1. Synthesis of ((N$_3$-EG$_4$)$_2$-EG$_4$)$_2$-NH-tBoc

Toluene (60 mL) was added to 3-Boc-NH-1,2-propanediol (0.78 g), then NaH (60%, 0.36 g) was added under an ice-water bath and reacted at room temperature for 2 hours; a toluene solution (30 mL) containing (N$_3$-EG$_4$)$_2$-EG$_4$-OH ((3), prepared in Example 1, 7.3 g) was added dropwise, and reacted at 60° C. overnight; then HPLC detection was carried out, and the toluene was evaporated to dryness; the remaining was added with DCM and water and washed once respectively, and then the DCM was evaporated to dryness to obtain a crude product. The crude product was recrystallized by ice diethyl ether twice to obtain 4.5 g of product (with a yield of 73%).

2. Synthesis of ((N$_3$-EG$_4$)$_2$-EG$_4$)$_2$-NHCO—C$_2$H$_4$—COOH

TFA (13 mL) and methylene chloride (27 mL) were added to ((N$_3$-EG$_4$)$_2$-EG$_4$)$_2$-NH-tBoc (4 g) and stirred at room temperature overnight; a solvent was evaporated to dryness, then the remaining was recrystallized by ice diethyl ether twice to obtain an intermediate. Then methylene chloride (35 mL) and triethylamine (0.5 mL) were added a and stirred evenly; then succinic anhydride (400 mg) was added, and reacted at room temperature overnight; then the remaining was washed with saturated brine (pH=5) once and recrystallized by ice diethyl ether twice to obtain 3 g of product (with a yield of 76%).

3. Synthesis of ((NH$_2$-EG$_4$)$_2$-EG$_4$)$_2$-NHCO—C$_2$H$_4$—COOH

DMF (20 mL) and triphenylphosphine (1.96 g) were added to ((N$_3$-EG$_4$)$_2$-EG$_4$)$_2$-NHCO—C$_2$H$_4$—COOH (2 mg) prepared in the step 2 above, reacted at room temperature overnight, then added with water (0.1 mL) and reacted overnight. The DMF was evaporated to dryness, then water (50 mL) was added, and the mixture was washed with ethyl acetate (40 mL) twice and DCM (30 mL) twice in sequence, then water was evaporated to dryness to obtain 1.4 g of product with a yield of 75%.

NMR(CDCl$_3$) δ: 2.4-2.6 (m, 4H, CH$_2$COOH), 2.8 (m, 8H, NH$_2$CH$_2$), 3.5-3.8 (m, 103H, other hydrogen excluding reactive hydrogen; ESI-MS: 1415.1 (M+Na)$^+$.

Example 8 Synthesis of Three Derivatives of Dendritic Molecule Derivative ((mEG$_3$)$_2$-N—C$_3$H$_6$)$_2$—N—C$_3$H$_6$—OH Cholesterol, hexadecanol and menthol derivatives of the ((mEG$_3$)$_2$-N—C$_3$H$_6$)$_2$—N—C$_3$H$_6$—OH were prepared respectively.

1. DCM (5 mL) and TEA (0.11 mL) were added to ((mEG$_3$)$_2$-N—C$_3$H$_6$)$_2$—N—C$_3$H$_6$—OH (0.4 g) prepared in Example 2, then cholesteryl chloroformate (0.3 g) was dissolved in DCM (5 mL), and added dropwise to a reaction flask. The mixture was stirred at room temperature overnight. The remaining was washed with water once, and then evaporated to dryness to obtain a crude product. The crude product was subjected to column purification (a MeOH/DCM system being a mobile phase, MeOH/DCM=0-7%) to obtain 190 mg of product (with a yield of 31%).

NMR(CDCl$_3$) δ: 5.55-5.45 (m, 1H), 4.65-4.50 (m, 1H), 4.1-4.0 (m, 2H), 3.5-3.8 (m, 40H), 3.37 (s, 12H), 2.7-2.8 (m, 12H), 2.50-0.80 (m, 46H), 0.65-0.60 (m, 3H).

2. DCM (5 mL) and TEA (0.11 mL) were added to ((mEG$_3$)$_2$-N—C$_3$H$_6$)$_2$—N—C$_3$H$_6$—OH (0.4 g) prepared in Example 2, then hexadecanol chloroformate (0.23 g) was dissolved in DCM (5 mL), and added dropwise to a reaction flask. The mixture was stirred at room temperature overnight. The reaction was detected to be complete through TLC, then the remaining was washed with water once, and evaporated to dryness to obtain a crude product. The crude product was subjected to column purification (6% MeOH/DCM) to obtain 150 mg of hexadecanol derivative (with a yield of 28%).

NMR(CDCl$_3$) R: 4.1-4.2 (m, 4H), 3.5-3.8 (m, 40H), 3.37 (s, 12H), 2.7-2.8 (m, 18H), 1.6-1.7 (m, 8H), 1.2-1.3 (m, 26H), 0.88 (t, 3H).

3. DCM (5 mL) and pyridine (0.11 mL) were added to ((mEG$_3$)$_2$-N—C$_3$H$_6$)$_2$—N—C$_3$H$_6$—OH (0.4 g) prepared in Example 2, then menthol chloroformate (0.17 g) was dissolved in DCM (5 mL), and added dropwise to a reaction flask. The mixture was stirred at room temperature overnight. The reaction was detected to be complete through TLC, then the remaining was washed with water once, and evaporated to dryness to obtain a crude product. The crude product was subjected to column purification (2% MeOH/DCM) to obtain 155 mg of menthol derivative (with a yield of 31%).

NMR(CDCl$_3$) R: 4.4 (m, 1H), 4.0-4.2 (m, 2H), 3.5-3.8 (m, 40H, OCH2), 3.37 (s, 12H, CH3O), 2.7-2.8 (m, 18H, N(CH2)$_3$), 2.0 (m, 1H), 1.82 (m, 1H), 1.6-1.7 (m, 9H), 1.4 (m, 4H), 1.0 (m, 9H).

Example 9 Synthesis of Three Derivatives of Linear-Chain Molecule Derivative mEG$_7$-OH Three derivatives of the mEG$_7$-OH were prepared using commercially available mEG$_7$-OH under the same conditions as in Example 8.

Cholesterol derivative: NMR(CDCl$_3$) δ: 5.45-5.55 (m, 1H), 4.50-4.65 (m, 1H), 4.0-4.1 (m, 2H), 3.5-3.8 (m, 26H), 3.37 (s, 3H), 0.80-2.50 (m, 40H), 0.60-0.65 (m, 3H).

Hexadecanol derivative: NMR(CDCl$_3$) δ: 4.27 (t, 2H), 4.12 (t, 2H), 3.5-3.8 (m, 26H), 3.38 (s, 3H), 1.65 (m, 2H), 1.25 (m, 26H), 0.88 (t, 3H).

Menthol derivative: NMR(CDCl$_3$) δ: 4.4-4.6 (m, 1H), 4.2-4.3 (m, 2H), 3.5-3.8 (m, 26H), 3.38 (s, 3H), 1.9-2.1 (m, 2H), 1.0-1.7 (m, 7H), 0.7-0.9 (m, 9H).

Example 10 Comparison of Solubility of Two Cholesterol Derivatives in Water 50.0 mg of the cholesterol derivative of the ((mEG$_3$)$_2$-N—C$_3$H$_6$)$_2$—N—C$_3$H$_6$—OH prepared in Example 8 was dispersed in 50 mL of water, and 5 mL of the mixture was taken out and added with 1.5 mL of water. Then the solution was shaken vigorously every 5 minutes for 30 seconds. After 30 minutes, the solution was turbid. Another 1.5 mL of water was added and the solution was shaken vigorously every 5 minutes for 30 seconds, and the solution became clear until 9 mL of water was totally added.

24.2 mg of the cholesterol derivative of the mEG$_7$-OH prepared in Example 9 was dispersed in 50 mL of water, and 5 mL of the mixture was taken out and added with 1.5 mL of water. Then the solution was shaken vigorously every 5 minutes for 30 seconds. After 30 minutes, the solution became turbid. Another 5 mL of water was added and the solution was shaken vigorously every 5 minutes for 30 seconds until 25 mL of water was totally added. 5 mL of the solution was taken out from the diluted solution and operated similarly, and the solution became clear until 10 mL of water was added.

Results are shown in Table 1. Analysis of the results shows that the solubility of the cholesterol derivative of the dendritic molecule ((mEG$_3$)$_2$-N—C$_3$H$_6$)$_2$—N—C$_3$H$_6$—OH is 35.7 mg/100 g H$_2$O, which is 13.3 times the solubility (2.69 mg/100 g H$_2$O) of the cholesterol derivative of the mEG$_7$-OH, and 178 times the solubility of cholesterol (less than 0.2 mg/100 g H$_2$O).

Example 11 Comparison Test of Solubility of Two Hexadecanol Derivatives in Water 111.0 mg of the hexadecanol derivative of the ((mEG$_3$)$_2$-N—C$_3$H$_6$)$_2$—N—C$_3$H$_6$—OH prepared in Example 8 was dispersed in 50 μL of water, and shaken vigorously every 5 minutes for 30 seconds. After 30 minutes, the solution became clear. Another 50 μL of water was added and the solution was shaken vigorously every 5 minutes for 30 seconds, and the solution was still clear until 1.025 mL of water was added.

112.9 mg of the hexadecanol derivative of the mEG$_7$-OH prepared in Example 9 was dispersed in 50 μL of water, and shaken vigorously every 5 minutes for 30 seconds. After 30 minutes, the solution was turbid. Another 50 μL of water was added and the solution was shaken vigorously every 5 minutes for 30 seconds, and the solution became clear until 250 μL of water was added.

Results are shown in Table 1. Analysis of the results shows that the solubility of the hexadecanol derivative of the dendritic molecule ((mEG$_3$)$_2$-N—C$_3$H$_6$)$_2$—N—C$_3$H$_6$—OH can be miscible with water in any ratio at room temperature, while the solubility of the hexadecanol derivative of the mEG$_7$-OH is 45.2 g/100 g H$_2$O, and the solubility of hexadecanol is less than 1 mg/100 g H$_2$O.

Example 12 Comparison of Solubility of Two Menthol Derivatives in Water 106.7 mg of the menthol derivative of the ((mEG$_3$)$_2$-N—C$_3$H$_6$)$_2$—N—C$_3$H$_6$—OH prepared in Example 8 was dispersed in 50 μL of water, and shaken vigorously every 5 minutes for 30 seconds. After 30 minutes, the solution was clear. Another 50 μL of water was added and the solution was shaken vigorously every 5 minutes for 30 seconds, and the solution was still clear until 1.025 mL of water was added.

101.3 mg of the menthol derivative of the mEG$_7$-OH prepared in Example 9 was dispersed in 50 μL of water, and shaken vigorously every 5 minutes for 30 seconds. After 30 minutes, the solution was turbid. Another 50 μL of water was added and the solution was shaken vigorously every 5 minutes for 30 seconds. After 30 minutes, the solution became clear.

Results are shown in Table 1. Analysis of the results shows that the solubility of the menthol derivative of the dendritic molecule ((mEG$_3$)$_2$-N—C$_3$H$_6$)$_2$—N—C$_3$H$_6$—OH can be miscible with water in any ratio at room temperature, while the solubility of the menthol derivative of the mEG$_7$-OH is 67.5 g/100 g H$_2$O, and the solubility of menthol is less than 100 mg/100 g H$_2$O.

TABLE 1

| | Solubility of three derivatives | | |
|---|---|---|---|
| Modifier | Cholesterol | Hexadecanol | Menthol |
| None | Less than 0.2 mg/ 100 g H$_2$O | Less than 1 mg/ 100 g H$_2$O | Less than 100 mg/ 100 g H$_2$O |
| mEG$_7$-OH | 2.69 mg/ 100 g H$_2$O | 45.2 g/ 100 g H$_2$O | 67.5 g/ 100 g H$_2$O |
| Dendritic molecule (prepared in Example 2) | 35.7 mg/ 100 g H$_2$O | Miscible with water in any ratio | Miscible with water in any ratio |

Those described above are merely preferred examples of the disclosure, but are not intended to limit the disclosure. Any modifications and equivalent substitutions made without departing from the principle of the disclosure shall all fall within the scope of protection of the disclosure.

What is claimed is:
1. A dendritic polyethylene glycol derivative having a structure of formula (I):

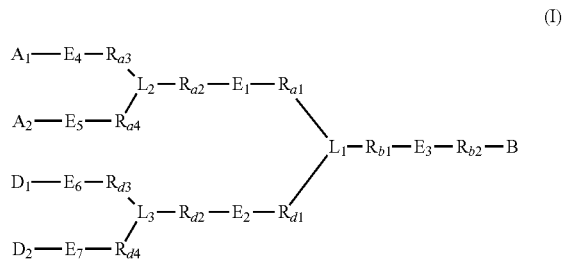

wherein,
A$_1$, A$_2$, D$_1$ and D$_2$ are Y-X-structures, which are the same or different, or

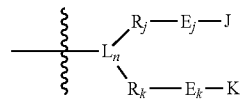

structures, which are the same or different;
J and K are Y-X-structures, which are the same or different;
R$_{a1}$, R$_{a2}$, R$_{a3}$, R$_{a4}$, R$_{b1}$, R$_{b2}$, R$_{d1}$, R$_{d2}$, R$_{d3}$ and R$_{d4}$, as well as R$_j$ and R$_k$ are linking groups independently selected from one or a combination of several of —(CH$_2$)$_r$—, —(CR$_1$R$_2$)$_r$—, —(CH$_2$)$_r$NH—, —NHCO(CH$_2$)$_r$—, —(CH$_2$)$_r$CONH— and —CO(CH$_2$)$_r$—, and r is an integer of 0 to 30,
R$_1$ and R$_2$ are independently selected from one or a combination of several of —H, C1—C6 alkyl, —OR', —NHR', —N(R')$_2$, —CN, —F, —Cl, —Br, —I, —COR', —COOR', —OCOR', —CONHR' and —CON(R')$_2$, R' is selected from —H, C1—C6 alkyl, —F, —Cl, —Br and —I, and B is selected from one of —OH, —NH₂, —CH₂COOH, —CH₂CH₂COOH, —SH, —CH₂CH₂CHO and —CH₂CH₂CH₂CHO;

X is a linking group selected from one or a combination of more than two of —(CH₂)$_i$—, —(CH₂)$_i$NH—, —CO(CH₂)$_i$—, —(CH₂)$_i$OCOO—, —(CH₂)$_i$OCONH—, —(CH₂)$_i$NHCONH—, —OC(CH₂)$_i$COO—, —(CH₂)$_i$COO— and —(CH₂)$_i$CONH—, and i is an integer of 0 to 10;

Y is an end group selected from one of C1—C6 alkyl, C1—C6 alkoxy, H, hydroxyl, amino, aminomethyl, maleimide group, carboxyl, ester, sulfhydryl, succinimidyl carbonate, succinimidyl acetate, succinimidyl propionate, succinimidyl succinate, succinimidyl, dithiopyridyl, propionic acid, aldehyde group, thioester group, acrylic group, acryloxy, azido, glutaric group, hydrazide, alkynyl, p-nitrophenyl carbonate, isocyanato, silane, carboxymethyl, vinyl sulfone group and vitamin H residue;

$E_{1-7}$, $E_j$ and $E_k$ are polyethylene glycol groups (OCH₂CH₂)$_m$, which are the same or different, and m is an integer of 0 to 100;

$L_{1-3}$ and $L_n$ are branching points independently selected from one or a combination of more than two of structures of formulae (II) to (VIII):

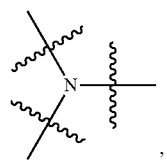
(II)

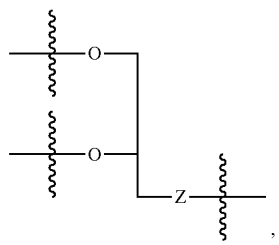
(III)

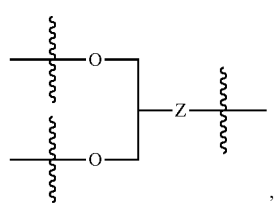
(IV)

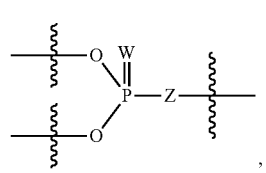
(V)

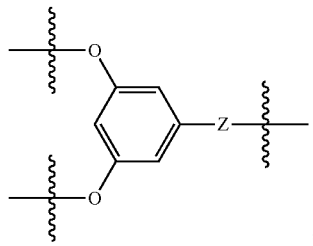
(VI)

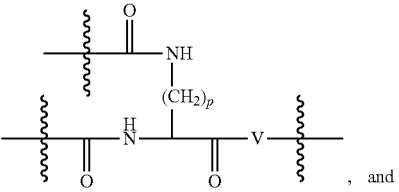
, and (VII)

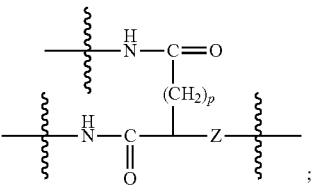
(VIII)

Z is selected from one of O, S, NH, NHCO, CO, COO, OC(O) and (CH₂)$_s$, and s is an integer of 0 to 10;

p is an integer of 0 to 10;

W is O or S; and

V is O or NH.

2. The derivative of claim 1, wherein the Z is selected from one of O, NH, NHCO and (CH₂)$_s$; and/or, the $R_{a1}$, the $R_{a2}$, the $R_{a3}$, the $R_{a4}$, the $R_{b1}$, the $R_{b2}$, the $R_{d1}$, the $R_{d2}$, the $R_{d3}$, the $R_{d4}$, the $R_j$ and the $R_k$ are —(CH₂)$_r$—, which are the same or different, and r is selected from an integer of 0 to 10.

3. The derivative of claim 1, wherein the $L_{1-3}$ and the $L_n$ are independently selected from

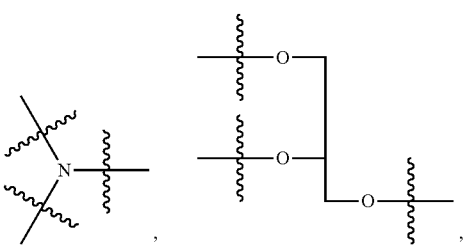
,

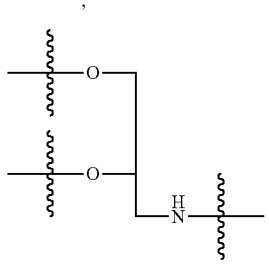
and

-continued

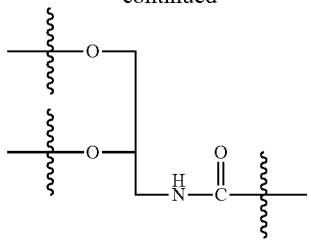

4. The derivative of claim 1, wherein the X is —(CH$_2$)$_i$—, —CO(CH$_2$)$_i$, —(CH$_2$)$_i$NH— or (CH$_2$)$_i$CONH—, and/or the i is 0, 1, 2, 3 or 4; and/or,
the Y is selected from one of methyl, methoxy, hydroxyl, amino, azido, sulfydryl, carboxyl, ester, aldehyde group, acrylic group and maleimide group.

5. The derivative of claim 1, wherein the A1, the A2, the D1 and the D2 are independently selected from one of —H, —CH$_3$, —OCH$_3$, —OH, —NH$_2$, —CH$_2$NH$_2$, —CH$_2$CH$_2$NH$_2$, —N$_3$, —CH$_2$N$_3$, —CH$_2$CH$_2$N$_3$, —CH$_2$COOH, —CH$_2$CH$_2$COOH, —SH, —CH$_2$CH$_2$CHO and —CH$_2$CH$_2$CH$_2$CHO.

6. The derivative of claim 1, wherein m in the polyethylene glycol group (OCH$_2$CH$_2$)$_m$ is an integer of 0 to 20.

7. The derivative of claim 1, wherein the dendritic polyethylene glycol derivative is selected from structures of following formulae (IX) to (IX):

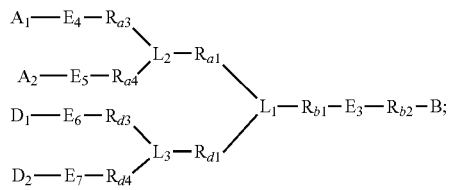
(IX)

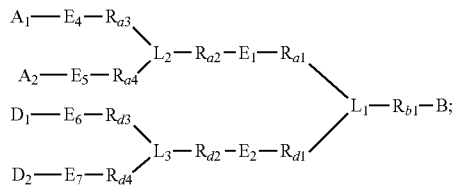
(X)

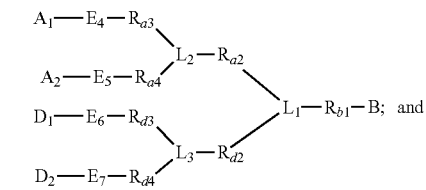
(XI)

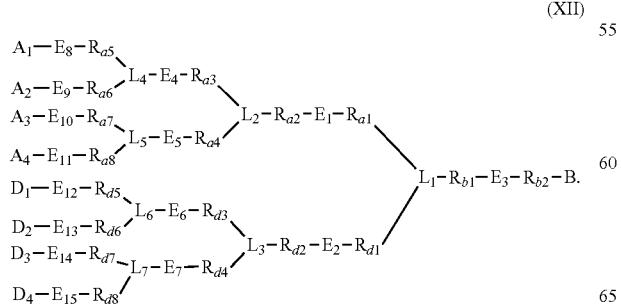
(XII)

8. The derivative of claim 1, wherein the dendritic polyethylene glycol derivative is selected from structures of following formulae (XIII) to (XVI):

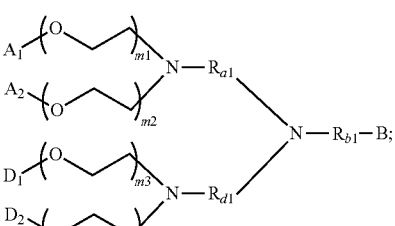
(XIII)

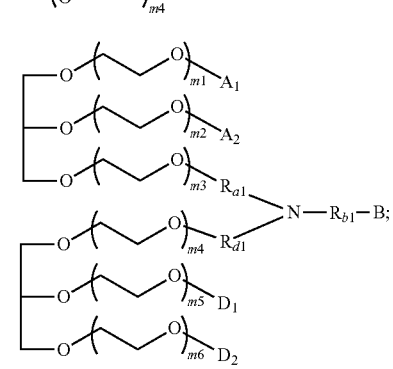
(XIV)

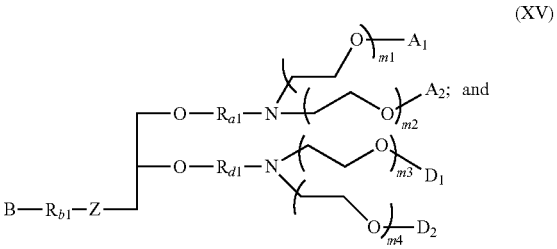
(XV)

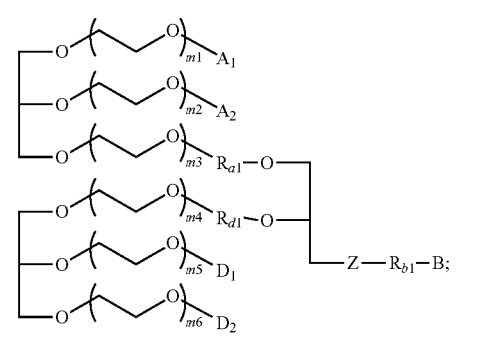
(XVI)

m1-6 is independently selected from an integer of 0 to 20; and/or,
in the A$_1$, the A$_2$, the D$_1$, the D$_2$ and the B, the X is selected from one or a combination of several of —(CH$_2$)$_i$—, —CO(CH$_2$)$_i$—, —(CH$_2$)$_i$NH— and (CH$_2$)$_i$CONH—; and/or,
in the A$_1$, the A$_2$, the D$_1$, the D$_2$ and the B, the Y is selected from one of methoxy, hydroxyl, amino, azido, sulfydryl, carboxyl, ester, aldehyde group, acrylic group and maleimide group; and/or,
the R$_{a1}$, the R$_{b1}$ and the R$_{d1}$ are —(CH$_2$)$_r$—, which are the same or different, and r is selected from an integer of 0 to 10; and/or,
the Z is O or NHCO.

9. The derivative of claim 8, wherein the dendritic polyethylene glycol derivative has structures of following formulae:

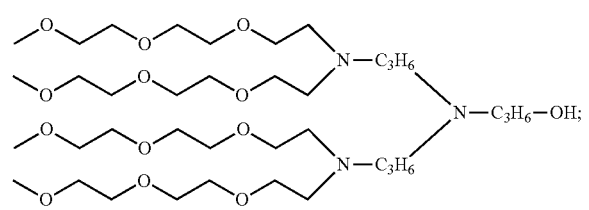
(XVI-1)

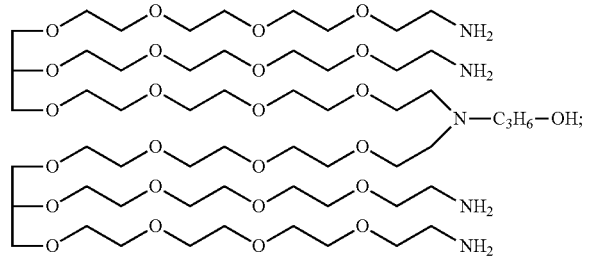
(XVII-1)

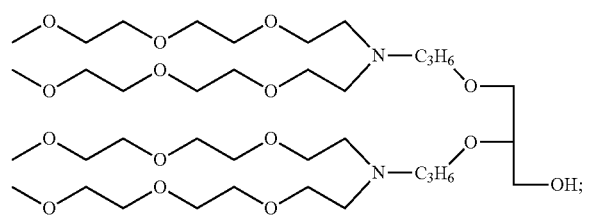
(XVIII-1)

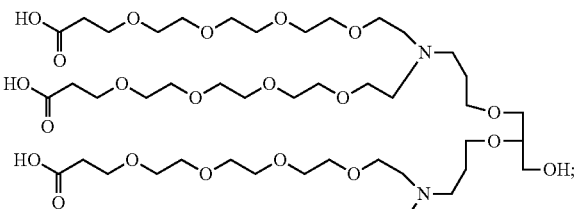
(XVIII-2)

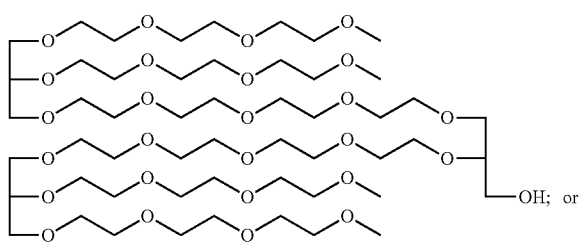
(XIX-1)

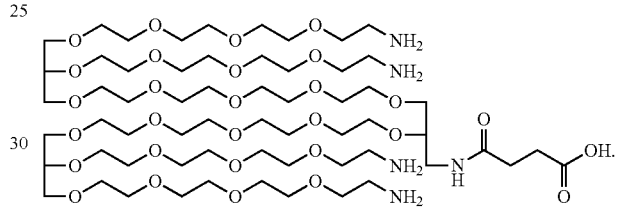
(XIX-2)

10. A covalent conjugate, comprising the dendritic polyethylene glycol derivative of claim 1 and a drug molecule, which are linked by a covalent bond.

11. The derivative of claim 6, wherein m in the polyethylene glycol group $(OCH_2CH_2)_m$ is an integer of 0 to 12.

12. The derivative of claim 11, wherein m in the polyethylene glycol group $(OCH_2CH_2)_m$ is 0, 1, 2, 3, 4, 5, 6, 7 or 8.

13. The derivative of claim 8, wherein m1-6 is independently selected from an integer of 0 to 12.

14. The derivative of claim 8, wherein m1-6 is independently selected from 0, 1, 2, 3, 4, 5, 6, 7 or 8.

* * * * *